United States Patent [19]

Dyer et al.

[11] Patent Number: 5,795,921
[45] Date of Patent: Aug. 18, 1998

[54] FOAMS MADE FOR HIGH INTERNAL PHASE EMULSIONS USEFUL AS ABSORBENT MEMBERS FOR CATAMENIAL PADS

[75] Inventors: John Collins Dyer, Cincinnati; Susan Nicole Lloyd, Middletown, both of Ohio

[73] Assignee: The Procter & Gamble Co., Cincinnati, Ohio

[21] Appl. No.: 688,496

[22] Filed: Jul. 30, 1996

Related U.S. Application Data

[60] Division of Ser. No. 542,497, Oct. 13, 1995, which is a continuation-in-part of Ser. No. 370,697, Jan. 10, 1995, abandoned.

[51] Int. Cl.$^6$ ............... C08J 9/28; A61F 13/15
[52] U.S. Cl. ............... 521/146; 521/62; 521/63; 521/64; 604/358; 604/369
[58] Field of Search ............... 521/62, 63, 64, 521/146; 604/358, 369

[56] References Cited

U.S. PATENT DOCUMENTS

| | | | |
|---|---|---|---|
| 3,255,127 | 6/1966 | Leverkusen et al. | 260/2.5 |
| 3,256,219 | 6/1966 | Will | 260/2.5 |
| 3,431,911 | 3/1969 | Meisel, Jr. | 128/287 |
| 3,563,243 | 2/1971 | Lindquist | 128/287 |
| 3,565,817 | 2/1971 | Lissant | 252/312 |
| 3,640,753 | 2/1972 | Krauch et al. | 117/62.2 |
| 3,734,867 | 5/1973 | Will | 260/2.5 R |
| 3,763,056 | 10/1973 | Will | 260/2.5 L |
| 3,778,390 | 12/1973 | Ulrich, Jr. | 260/2.5 AN |
| 3,806,474 | 4/1974 | Blair | 260/2.5 AG |
| 3,988,508 | 10/1976 | Lissant | 526/344 |
| 3,993,074 | 11/1976 | Murray et al. | 128/286 |
| 3,994,298 | 11/1976 | DesMarais | 128/285 |
| 4,029,100 | 6/1977 | Karami | 128/284 |
| 4,049,592 | 9/1977 | Marans et al. | 260/2.5 AD |
| 4,061,145 | 12/1977 | DesMarais | 128/275 |
| 4,067,832 | 1/1978 | DesMarais | 260/2.5 AB |
| 4,093,570 | 6/1978 | Miyake et al. | 260/2.6 B |
| 4,110,276 | 8/1978 | DesMarais | 521/123 |
| 4,132,839 | 1/1979 | Marans et al. | 521/159 |
| 4,262,052 | 4/1981 | Kannan et al. | 428/306 |
| 4,376,440 | 3/1983 | Whitehead et al. | 604/387 |
| 4,394,930 | 7/1983 | Korpman | 220/444 |
| 4,425,130 | 1/1984 | DesMarais | 604/389 |
| 4,473,611 | 9/1984 | Haq | 428/198 |
| 4,522,953 | 6/1985 | Barby et al. | 521/64 |
| 4,536,521 | 8/1985 | Haq | 521/146 |
| 4,540,717 | 9/1985 | Mahnke et al. | 521/52 |
| 4,554,297 | 11/1985 | Dabi | 521/178 |
| 4,603,069 | 7/1986 | Haq et al. | 428/76 |
| 4,606,958 | 8/1986 | Haq et al. | 428/68 |
| 4,611,014 | 9/1986 | Jones et al. | 521/146 |
| 4,612,334 | 9/1986 | Jones et al. | 521/146 |
| 4,613,543 | 9/1986 | Dabi | 428/304.4 |
| 4,668,709 | 5/1987 | Jones et al. | 521/146 |
| 4,724,242 | 2/1988 | Vassileff | 521/83 |
| 4,725,628 | 2/1988 | Garvey et al. | 521/137 |
| 4,731,391 | 3/1988 | Garvey | 521/137 |
| 4,740,528 | 4/1988 | Garvey et al. | 521/128 |
| 4,775,655 | 10/1988 | Edwards et al. | 502/416 |
| 4,788,225 | 11/1988 | Edwards et al. | 521/147 |
| 4,797,310 | 1/1989 | Barby et al. | 428/71 |
| 4,839,395 | 6/1989 | Masamizu et al. | 521/56 |
| 4,957,810 | 9/1990 | Eleouet et al. | 428/306.6 |
| 4,959,341 | 9/1990 | Wallach | 502/404 |
| 4,961,982 | 10/1990 | Taylor | 428/41 |
| 4,965,289 | 10/1990 | Sherrington et al. | 521/53 |
| 4,966,919 | 10/1990 | Williams, Jr. et al. | 521/54 |

(List continued on next page.)

FOREIGN PATENT DOCUMENTS

| | | |
|---|---|---|
| 0 017 671 A1 | 10/1980 | European Pat. Off. . |
| 0 017 672 A1 | 10/1980 | European Pat. Off. . |
| 0 049 768 A1 | 4/1982 | European Pat. Off. . |
| 0 299 762 | 1/1989 | European Pat. Off. . |
| 0 480 379 A2 | 4/1992 | European Pat. Off. . |
| 1340520 | 9/1963 | France . |
| 1340520 | 9/1993 | France . |
| 3 109 929 A1 | 1/1982 | Germany . |
| Het 2-239863 | 9/1990 | Japan . |
| Hei 2-289608 | 11/1990 | Japan . |
| 3-49759 | 3/1991 | Japan . |
| 1 493 356 | 11/1977 | United Kingdom . |
| 2 078 527 | 1/1982 | United Kingdom . |
| 2 188 055 A | 9/1987 | United Kingdom . |
| WO 94/28839 | 12/1994 | WIPO . |

OTHER PUBLICATIONS

Structure of High Internal Phase Ratio Emulsions, Lissant, pp. 416–423, 1974.
A Study of Medium and High Internal Phase Ratio Water/Polymer Emulsions, Lissant, pp. 201–108, 1973.
The Geometry of High–Internal–Phase Ratio Emulsions, Lissant, pp. 462–468 1966.
Low Density, Microcellular polystyrene foams, Aubert and Clough, pp. 2047–2054, 1985.
Mechanical Structure Property Relationships of Microcellulsr, Low Density Foams, LeMay, pp. 21–26, 1991.
New Melamine–based elastic foam, Weber and Kruckau, pp. 843–848, 1985.
Preparation of multishell ICF target plastic foam cushion materials by thermally induced phase inversion processes, Young, Moreno and Marsters, pp.1094–2004, 1981.
Cellular Solids Structure & Properties, Gibson and Ashby, pp. 120–200, 1988.

*Primary Examiner*—Morton Foelak
*Attorney, Agent, or Firm*—Eric W. Guttag; Carl J. Roof; E. Kelly Linman

[57] ABSTRACT

Foams capable of absorbing blood and blood-based fluids, especially menses. These absorbent foams have high capillary absorption pressures required of absorbents used in catamenial products, yet have sufficient openness to allow free movement of the insoluble components in blood-based fluids such as menses. These absorbent foams are made by polymerizing high internal phase emulsions (HIPEs) where the volume to weight ratio of the water phase to the oil phase is in the range of from about 20:1 to about 125:1. These foams are particularly useful as absorbent members for catamenial pads.

9 Claims, 5 Drawing Sheets

U.S. PATENT DOCUMENTS

| | | | |
|---|---|---|---|
| 4,985,467 | 1/1991 | Kelly et al. | 521/52 |
| 4,985,468 | 1/1991 | Elmes et al. | 521/63 |
| 4,990,541 | 2/1991 | Nielsen et al. | 521/70 |
| 4,992,254 | 2/1991 | Kong | 423/449 |
| 5,021,462 | 6/1991 | Elmes et al. | 521/63 |
| 5,037,859 | 8/1991 | Williams, Jr. et al. | 521/55 |
| 5,047,225 | 9/1991 | Kong | 423/447.2 |
| 5,065,752 | 11/1991 | Sessions et al. | 128/156 |
| 5,066,684 | 11/1991 | LeMay | 521/64 |
| 5,066,784 | 11/1991 | Sherrington et al. | 530/334 |
| 5,110,838 | 5/1992 | Tokiwa et al. | 521/81 |
| 5,116,880 | 5/1992 | Tokiwa et al. | 521/134 |
| 5,116,883 | 5/1992 | LeMay | 521/178 |
| 5,128,382 | 7/1992 | Elliott, Jr. et al. | 521/178 |
| 5,134,007 | 7/1992 | Reising et al. | 428/78 |
| 5,134,171 | 7/1992 | Hammel et al. | 521/98 |
| 5,147,345 | 9/1992 | Young et al. | 604/378 |
| 5,149,720 | 9/1992 | DesMarais et al. | 521/63 |
| 5,189,070 | 2/1993 | Brownscombe et al. | 521/64 |
| 5,198,472 | 3/1993 | DesMarais et al. | 521/63 |
| 5,200,433 | 4/1993 | Beshouri | 521/64 |
| 5,210,104 | 5/1993 | Bass et al. | 521/64 |
| 5,210,108 | 5/1993 | Spinu et al. | 521/182 |
| 5,221,726 | 6/1993 | Dabi et al. | 528/93 |
| 5,250,576 | 10/1993 | Des Marais et al. | 521/63 |
| 5,252,619 | 10/1993 | Brownscombe et al. | 521/64 |
| 5,260,345 | 11/1993 | DesMarais et al. | 521/148 |
| 5,268,224 | 12/1993 | DesMarais et al. | 428/286 |
| 5,290,820 | 3/1994 | Brownscombe et al. | 521/64 |
| 5,318,554 | 6/1994 | Young et al. | 604/378 |
| 5,331,015 | 7/1994 | DesMarais et al. | 521/62 |
| 5,336,208 | 8/1994 | Rosenbluth et al. | 604/329 |
| 5,336,695 | 8/1994 | Nass et al. | 521/109.1 |
| 5,352,711 | 10/1994 | DesMarais | 521/149 |
| 5,387,207 | 2/1995 | Dyer et al. | 604/369 | ns
FOAMS MADE FOR HIGH INTERNAL PHASE EMULSIONS USEFUL AS ABSORBENT MEMBERS FOR CATAMENIAL PADS

This is a division of application Ser. No. 08/542,497, filed on Oct. 13, 1995, which is a continuation-in-part of application Ser. No. 08/370,697, filed on Jan. 10, 1995.

FIELD OF THE INVENTION

This application relates to flexible, microporous, open-celled polymeric foam materials made from high internal phase emulsions that can absorb blood and blood-based fluids such as menses. This application particularly relates to absorbent foam materials that are useful as absorbent members for catamenial pads, tampons, bandages, wound dressings, surgical drapes and the like.

BACKGROUND OF THE INVENTION

The development of highly absorbent articles for blood and blood-based fluids such as catamenial pads (e.g., sanitary napkins), tampons, wound dressings, bandages and surgical drapes can be challenging. Compared to water and urine, blood and blood based fluids such as menses are relatively complex mixtures of dissolved and undissolved components (e.g., erythrocytes or red blood cells). In particular, blood-based fluids such as menses are much more viscous than water and urine. This higher viscosity hampers the ability of conventional absorbent materials to efficiently and rapidly transport these blood-based fluids to regions remote from the point of initial discharge. Undissolved elements in these blood-based fluids can also potentially clog the capillaries of these absorbent materials. This makes the design of appropriate absorbent systems for blood-based fluids such as menses particularly difficult.

In the case of catamenial pads, women have come to expect a high level of performance in terms of comfort and fit, retention of fluid, and minimal staining. Above all, leakage of fluid from the pad onto undergarments is regarded as totally unacceptable. Improving the performance of such catamenial pads continues to be a formidable undertaking, although a number of improvements have been made in both catamenial structures, and materials used in such structures. However, eliminating leakage, particularly along the inside of the thighs, without compromising fit and comfort, has not always met the desired needs of the consumer.

The users of sanitary napkins, and the like, have also come to expect the surface of such products to provide a cleaner, more sanitary and drier aspect than common cloth or nonwoven materials have historically provided. Current sanitary napkin products are typically provided with nonwoven or formed-film permeable topsheets that are designed to move discharged menstrual fluids rapidly through and into an underlying absorbent structure. This rapid movement of acquired menstrual fluids is designed to provide a drier and cleaner surface adjacent the wearer of the product.

The absorbent structures of current catamenial (e.g., sanitary napkin) pads have typically comprised one or more fibrous layers for acquiring the discharged menstrual fluid from the permeable topsheet and distributing it to an underlying storage area. Absorbent structures for relatively thin versions of prior catamenial products usually comprise a fluid acquisition layer (often called a "secondary topsheet") that is adjacent to the permeable topsheet. This "secondary topsheet" typically is made from an air-laid-tissue web or a synthetic nonwoven. Underlying this secondary topsheet is the main absorbent core that is typically made from air-laid or wet-laid tissue. The absorbent core often contains a particulate absorbent gelling material that can be encased or enveloped within this tissue. Such encased or enveloped cores are often referred to as tissue laminate cores. See, for example, U.S. Pat. No. 4,950,264 (Osborn), issued Aug. 21, 1990 and U.S. Pat. No. 5,009,653 (Osborn), issued Apr. 23, 1991, that disclose tissue laminate cores used in sanitary napkin products.

Prior catamenial absorbent structures made from fibrous layers have a number of problems. One is the difficulty in ensuring adequate topsheet dryness. In particular, the acquired menstrual fluid can potentially leak back through the main topsheet. This phenomenon is often referred to as "rewet." Rewet can be significantly reduced by increasing the fluid capillary pressure exerted by the absorbent core for fluid relative to the main and secondary topsheet. The greater the disparity in fluid capillary pressure between core and topsheet elements, the greater the potential for providing a dry topsheet surface in contact with the body. This potential, however, can only be realized if the kinetics of fluid movement throughout the core is sufficiently fast.

Prior catamenial absorbent structures, and in particular catamenial pads using such structures, have also had a greater chance of causing panty and body soiling. This is because the absorbent structure lacks resilience, leading to bunching of the pad. This lack of resilience, and consequent bunching, has also caused these prior catamenial pads to provide poorer fit and comfort for the user.

An alternative to conventional catamenial absorbent structures are absorbent foams. Absorbent foams can possess desirable wet integrity, can provide suitable fit throughout the entire period the article is worn, and can minimize changes in shape during use (e.g., uncontrolled swelling, bunching, etc.). In addition, catamenial products containing such foam structures can be easier to manufacture on a commercial scale. For example, absorbent cores can simply be stamped out from continuous foam sheets and can be designed to have considerably greater integrity and uniformity than conventional absorbent fibrous webs. Such foams can also be prepared in any desired shape, or even formed into single-piece catamenial pad, or other absorbent article used to absorb blood or blood-base fluids such as tampons, wound dressings, bandages and surgical drapes.

Foams of various types have been suggested for use in tampons, sanitary napkins and other articles that absorb blood and blood-based fluids. See for example U.S. Pat. No. 4,110,276 (DesMarais), issued Aug. 29, 1978 (soft, flexible, open celled foams made from polyurethanes, cellulose, or styrene/butadiene rubber that can be used in tampons and sanitary pads); U.S. Pat. No. 4,752,349 (Gebel), issued Jun. 21, 1988 (foams of "medium cell size" hydrophilized by surfactant treatment and having a density within the range of 0.1 to 0.8 g/cc); U.S. Pat. No. 4,613,543 (Dabi), issued Sep. 18, 1986 (hydrophilic cellular polymers used in catamenial products); U.S. Pat. No. 3,903,232 (Wood et al.), issued Sep. 2, 1975 (compressed hydrophilic polyurethane foams useful in biomedical applications, including catamenial devices); U.S. Pat. No. 4,049,592 (Marans et al.) issued Sep. 20, 1977 (biodegradable hydrophilic polyurethane foams highly absorptive upon contact with liquids or bodily fluids having utility in sanitary napkins and the like). Prior foams used in these products have tended to have relatively large cell sizes. As a result, these prior foams do not exert sufficient fluid capillary pressure for blood and blood-based fluids to acquire discharged menstrual fluids quickly from and through the topsheet of catamenial products such as sanitary napkins. This results in undesirable rewet since the surface in immediate contact with the body retains some of the fluid that is not absorbed into the core and is available to be transferred back onto the body of the wearer.

Suitable absorbent foams for absorbent products have also been made from High Internal Phase Emulsions (hereafter referred to as "HIPE"). See, for example, U.S. Pat. No. 5,260,345 (DesMarais et al), issued Nov. 9, 1993 and U.S. Pat. No. 5,268,224 (DesMarais et al), issued Dec. 7, 1993. These absorbent HIPE foams provide desirable fluid handling properties, including: (a) relatively good wicking and fluid distribution characteristics to transport fluid away from the initial impingement zone and into the unused balance of the foam structure to allow for subsequent gushes of fluid to be accommodated; and (b) a relatively high storage capacity with a relatively high fluid capacity under load, i.e. under compressive forces. These HIPE absorbent foams are also sufficiently flexible and soft so as to provide a high degree of comfort to the wearer of the absorbent article; some of these foams can be made relatively thin until subsequently wetted by the absorbed body fluids. See also U.S. Pat. No. 5,147,345 (Young et al), issued Sep. 15, 1992 and U.S. Pat. No. 5,318,554 (Young et al), issued Jun. 7, 1994, which disclose absorbent cores having a fluid acquisition/ distribution component that can be a hydrophilic, flexible, open-celled foam such as a melamine-formaldehyde foam (e.g., BASOTECT made by BASF), and a fluid storage/ redistribution component that is a HIPE-based absorbent foam.

HIPE foams can provide the fluid capillary pressure necessary to remove most of the menstrual fluid from the body, or topsheet adjacent to the body, thus minimizing rewet. However, it has been found that the residual hydratable salts such as calcium chloride typically present in prior HIPE foams can impair the rapid acquisition blood and blood-based fluids by these foams, and especially the wicking of such fluids within these foams. As noted above, blood and blood-based fluids such as menses are more highly viscous than water and especially urine. The higher viscosity of these fluids is further increased by the presence of these salts. Moreover, prior HIPE foams typically have a foam microstructure too small to admit readily the undissolved components of blood and blood-based fluids such as red blood cells.

Accordingly, it would be desirable to be able to make an open-celled absorbent polymeric foam material, in particular an absorbent HIPE foam, that: (1) can rapidly absorb blood and blood-based fluids such as menses; (2) can be used as absorbent members for relatively thin catamenial pads (e.g., sanitary napkins) and other catamenial products such as tampons, as well as wound dressings, bandages, surgical drapes and the like; (3) allow storage components having higher capillary or osmotic absorption pressures to partition away this fluid; (4) keep the source of the blood-based fluids relatively free of rewet, even in "gush" situations and under compressive load; (5) are soft, flexible, resilient, and comfortable to the wearer of the absorbent article, and (6) have a relatively high capacity for fluid to provide efficient in their utilization of costly components.

While thin catamenial products are desired by many users, there is significant demand for relatively thick products. For example, a thick product may provide a perceived ability to better absorb and retain fluid. Also, a thick product may offer improved fit. It would therefore be desirable to have a relatively thin absorbent foam material(s) as the absorbent core of a catamenial product that allows the use of inexpensive filler materials (e.g., airfelt) to provide bulk/ thickness.

DISCLOSURE OF THE INVENTION

The present invention relates to polymeric foam materials that are capable of absorbing blood and blood-based fluids such as menses and then moving these absorbed fluids efficiently to other regions of the foam. These absorbent polymeric foam materials comprise a hydrophilic, flexible, nonionic polymeric foam structure of interconnected open-cells. This foam structure has:

A) the ability to wick artificial menstrual fluid (AMF) vertically to a height of 5 cm in less than about 60 minutes;

B) a capillary specific surface area in the range of from about 0.0080 to about 0.040 $m^2/cc$;

C) a resistance to compression deflection of from about 5 to about 95% when measured under a confining pressure of 0.74 psi at 31° C. after 15 minutes;

D) a free absorbent capacity of from about 20 to about 125 g/g; and

E) less than about 2% of residual hydratable salts.

A particularly important attribute of the foams of the present invention is that the connecting passages (holes) between the cells of these foams are sufficiently large to pass insoluble solids such as erythrocytes (mean diameter 8 μm). As a result, these holes do not become blocked or obstructed by blood and blood-based fluids absorbed by the foam. Even though the cells and holes are large enough to allow free movement of insoluble components in blood and blood-based fluids, they are sufficiently small so as to produce the necessary high capillary absorption pressure required of absorbents used in catamenial products. In other words, these foams combine high capillary absorption pressure with sufficient openness to allow free movement of the insoluble components in blood and blood-based fluids such as menses. Typically, the cells of these foams have a number average cell size of from about 20 to about 180 μm, while the holes between these cells have a number average hole size of from about 4 to about 30 μm.

The present invention further relates to a process for obtaining these absorbent foams by polymerizing a specific type of water-in-oil emulsion or HIPE having a relatively small amount of an oil phase and a relatively greater amount of a water phase. This process comprises the steps of:

A) forming a water-in-oil emulsion at a temperature of about 50° C. or higher and under low shear mixing from:

1) an oil phase comprising:

a) from about 85 to about 98% by weight of a monomer component capable of forming a copolymer having a Tg of about 50° C. or lower, the monomer component comprising:

i) from about 45 to about 70% by weight of at least one substantially water-insoluble monofunctional monomer capable of forming an atactic amorphous polymer having a Tg of about 35° C. or lower, ii) from about 10 to about 40% by weight of at least one substantially water-insoluble monofunctional comonomer capable of imparting toughness about equivalent to that provided by styrene;

iii) from about 5 to about 25% by weight of a first substantially water-insoluble, polyfunctional crosslinking agent selected from divinyl benzenes, trivinyl benzenes, divinyl toluenes, divinyl xylenes, divinyl naphthalenes divinyl alkylbenzenes, divinyl phenanthrenes, divinyl biphenyls, divinyl diphenylmethanes, divinyl benzyls, divinyl phenylethers, divinyl diphenylsulfides, divinyl furans, divinyl sulfide, divinyl sulfone, and mixtures thereof; and iv) from 0 to about 15% by weight of a second substantially water-insoluble, polyfunctional crosslinking agent selected from polyfunctional acrylates, methacrylates, acrylamides, methacrylamides, and mixtures thereof; and b) from about 2 to about 15% by weight of an emulsifier component which is soluble in the oil phase and which is suitable for forming a stable water-in-oil emulsion, the emulsion component comprising:

(i) a primary emulsifier having at least about 40% by weight emulsifying components selected from diglycerol monoesters of linear unsaturated $C_{16}$–$C_{22}$ fatty acids, diglycerol monoesters of branched $C_{16}$–$C_{24}$ fatty acids, diglycerol monoaliphatic ethers of branched $C_{16}$–$C_{24}$ alcohols, diglycerol monoaliphatic ethers of linear unsaturated $C_{16}$–$C_{22}$ alcohols, diglycerol monoaliphatic ethers of linear saturated $C_{12}$–$C_{14}$ alcohols, sorbitan monoesters of linear unsaturated $C_{16}$–$C_{22}$ fatty acids, sorbitan monoesters of branched $C_{16}$–$C_{24}$ fatty acids, and mixtures thereof; or (ii) the combination a primary emulsifier having at least 20% by weight of these emulsifying components and certain secondary emulsifiers in a weight ratio of primary to secondary emulsifier of from about 50:1 to about 1:4; and 2) a water phase comprising an aqueous solution containing from about 0.2 to about 20% by weight of a water-soluble electrolyte;

3) a volume to weight ratio of water phase to oil phase in the range of from about 20:1 to about 125:1;

B) polymerizing the monomer component in the oil phase of the water-in-oil emulsion to form a polymeric foam material;

C) washing the polymeric foam material to lower the level of residual electrolytes less than about 2%;

D) treating the washed foam with an effective amount of a suitable hydrophilizing surfactant; and E) dewatering the washed foam to a moisture content of about 40% or less.

The process of the present invention allows these absorbent foams to have cells and holes small enough to provide a high capillary absorptive pressure but large enough to prevent or minimize blockage by the insoluble components of these fluids. In addition, this process removes most of the residual electrolytes (i.e., hydratable salts) from the foam. While these hydratable salts are typically needed during initial formation of the HIPE, their presence in the resulting foam can adversely affect its ability to absorb blood and blood-based fluids such as menses, especially as the concentration of these salts in the foam increases. Accordingly, it is desirable to reduce the level of these hydratable salts in the foam.

The present invention also relates to catamenial products containing one or more foam materials of the present invention as the absorbent core.

DETAILED DESCRIPTION OF THE INVENTION

1. Polymeric Absorbent Foams

A. General Foam Characteristics

Figure 1:
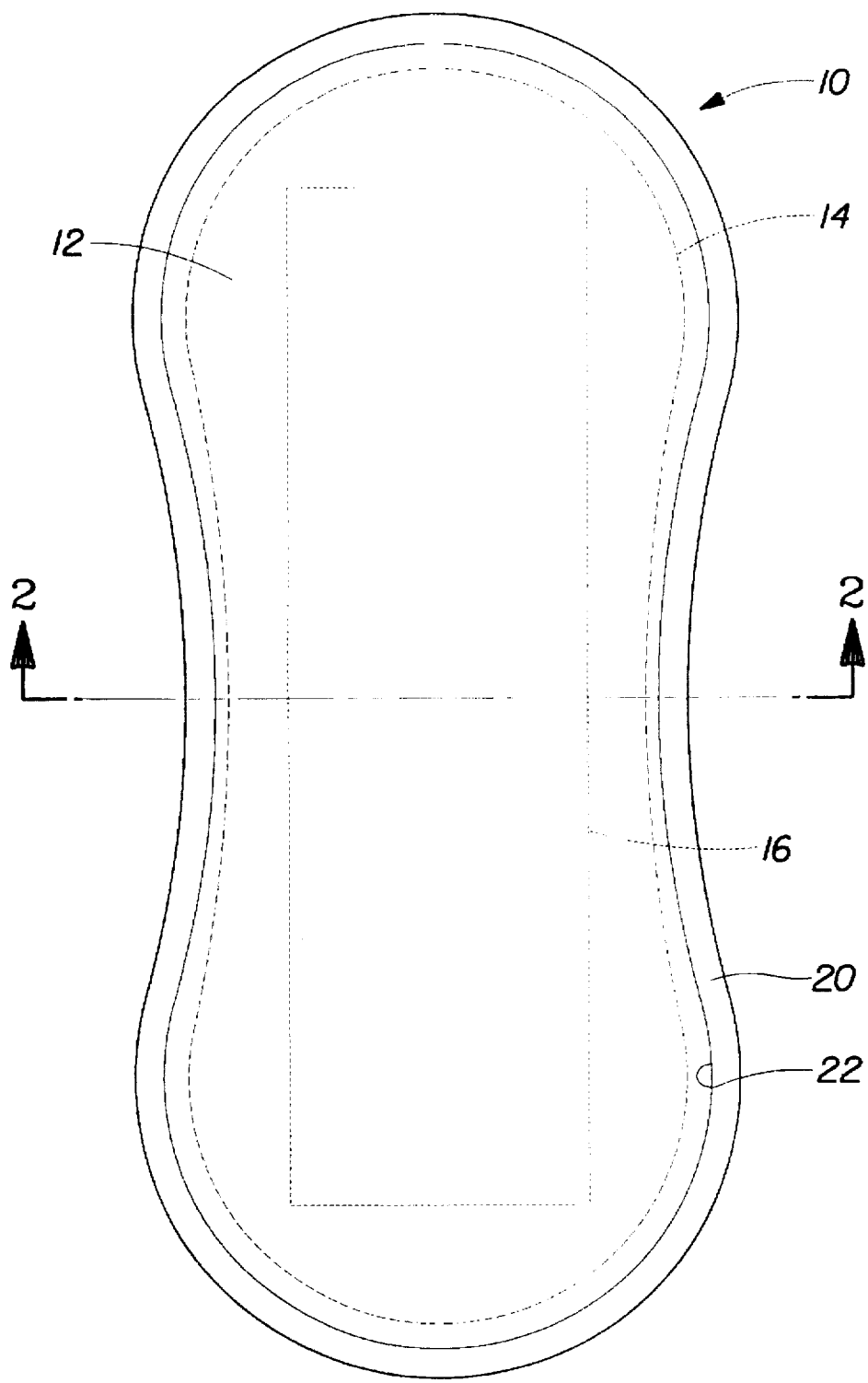
FIG. 1 of the drawings is a top-plan view of a catamenial product having HIPE foams of the present invention as absorbent members.

Polymeric foams according to the present invention useful in absorbent articles and structures are those which are highly open-celled. This means the individual cells of the foam are in complete, unobstructed communication with adjoining cells. The cells in such substantially open-celled foam structures have intercellular openings or "windows" (holes) that provide passageways large enough to permit free and ready movement of blood and blood based fluids such as menses from one cell to another within the foam structure, even though these fluids contain certain insoluble components. On the other hand, these cells and connecting passages are small enough to provide the necessary high capillary absorption pressure (i.e., capillary specific surface area per volume) to effectively move these fluids throughout the foam.

These substantially open-celled foam structures will generally have a reticulated character with the individual cells being defined by a plurality of mutually connected, three dimensionally branched webs. The strands of polymeric material making up these branched webs can be referred to as "struts." Open-celled foams having a typical strut-type structure are shown by way of example in the photomicrograph shown FIGS. 3. For purposes of the present invention, a foam material is "open-celled" if at least 80% of the cells in the foam structure are at least 1 µm size are in fluid communication with at least one adjacent cell.

In addition to being open-celled, these polymeric foams need to be rendered sufficiently hydrophilic to permit the foam to absorb blood and blood-based fluids. The internal surfaces of the foam structures are rendered hydrophilic by residual hydrophilizing surfactants left in the foam structure after polymerization, or by selected post-polymerization foam treatment procedures, as described hereafter.

The polymeric foams useful in the present invention also have somewhat interrelated and interdependent structural and mechanical properties, features and/or characteristics. It should be understood that these foams can have different properties, features and/or characteristics at different times prior to contact between the foam and the blood or blood based fluid to be absorbed. For example, during their manufacture, shipping, storage, etc., these foams can have density and/or cell size values outside the ranges set forth hereafter for these parameters, for example if they are stored in a collapsed state or are compressed by packaging. However, such foams are nevertheless still within the scope of this invention if they later undergo physical changes so that they have the requisite values specified hereafter for these properties, features and/or characteristics at least some point prior to and/or during contact with the blood or blood based fluid to be absorbed.

The foams of the present invention may also be used in their collapsed state similar to the condition described in U.S. Pat. No. 5,387,207 (Dyer et al.) issued Feb. 7, 1995. Such foams generally comprise those having finer microstructure (higher capillary specific surface areas) and which are relatively weak. These foams remain collapsed after washing, treating with wetting agents, and drying. Unlike the foams described within U.S. Pat. No. 5,387,207, the present foams may be reexpanded by application of modest amounts of heat (e.g. 60° C. for several hours). Or, they may be used so as to maintain the thinness of the product prior to use. When exposed to blood and blood-based fluids, these collapsed foams regain their original thickness and fluid capacities. These foams are also useful in distributing blood and blood-based fluids effectively from the point of insult since the fluid capillary pressure exerted by the unexpanded regions of these foams exceeds that of the wetted, expanded area of the foam. These materials generally serve well when positioned beneath a larger celled foam of the present invention which serves to acquire rapidly the blood and blood-based fluid. The properties of these collapsed foams stated herein are those of the foams in their expanded state unless otherwise noted.

B. Foam Characteristics Important to Absorbing and Transporting Blood and Blood-Based Fluids 1. Vertical Wicking Capability Vertical wicking (i.e., fluid wicking in a direction opposite from gravitational forces) of a given amount of fluid within a set period of time is an especially important performance attribute for absorbent foams herein. The rate of fluid wicking through a porous structure is generally a function of the openness of the structure, the affinity of the fluid for the surface of the structure, and the viscosity of the fluid. This is conveniently measured as the time taken for a test fluid, i.e., Artificial Menstrual Fluid (AMF), in a reservoir to wick a vertical distance of 5 cm through a test strip of foam of specified size at 22° C. Such a vertical wicking test is described hereafter in the TEST METHODS section. To be especially useful in catamenial products for absorbing menses, the foam absorbents of the present invention vertically wick the AMF 5 cm in less than about 60 minutes. More preferably, the preferred foam absorbents of the present invention vertically wick AMF 5 cm in less than about 20 minutes, and most preferably in less than about 15 minutes.

The foam absorbents of the present invention will also preferably wick a high capacity of the test fluid to a particular height at equilibrium. Preferably, these foams will wick at least about 30 g/g AMF (g of AMF/g dry foam) to a height of about 5 cm, more preferably at least about 40 g/g of AMF. Particularly preferred foam absorbents will wick at least about 45 g/g of AMF to a height of about 5 cm. The procedure for measuring the ability to wick fluid to a particular height at equilibrium is described hereafter in the TEST METHODS section.

2. Capillary Specific Surface Area

"Capillary suction specific surface area" is a measure of the test-liquid-accessible surface area of the polymeric network accessible to a test fluid. Capillary suction specific surface area is determined both by the dimensions of the cellular units in the foam and by the density of the polymer, and is thus a way of quantifying the total amount of solid surface provided by the foam network to the extent that such a surface participates in absorbency. For purposes of the present invention, capillary suction specific surface area is determined by the method is set forth in the TEST METHODS section of U.S. Pat. No. 5,387,207 (Dyer et al.) issued Feb. 7, 1995, which is incorporated by reference.

Generally, the surface area of the foam at a constant volume increases as the cellular structure becomes smaller celled ("finer"). Higher surface areas are highly desirable in rapidly moving blood and blood-based fluids such as menses within the foam. However, the surface area of the foam can reach the point that the rate of fluid absorption becomes limiting, as well as increasing the likelihood that insoluble components within the fluid can no longer pass readily from one cell to another. Accordingly, the surface area of the foam needs to be selected within a particular range to balance these competing factors. The polymeric foams of the present invention useful as absorbent members in catamenial products are those that have a capillary suction specific surface area in the range of from about 0.0080 to about 0.040 $m^2/cc$. Typically, the capillary suction specific surface area is in the range from about 0.010 to about 0.030 $m^2/cc$, preferably from about 0.012 to about 0.026 $m^2/cc$.

For absorbent cores where two layers of absorbent foam are used, it is preferred that the upper foam layer (facing the body of the wearer) have a lower capillary suction specific surface area, for example from about 0.012 to about 0.020 $m^2/cc$, while the lower foam layer has a higher capillary suction specific surface area, for example from about 0.020 to about 0.026 $m^2/cc$. In this way, the lower foam layer will have a higher fluid capillary pressure, allowing it to drain fluid from the upper foam layer, thus keeping the body of the wearer relatively free from contact with the fluid. (It follows that where more than two foam layers are employed, the capillary suction specific surface area of the respective foams preferably will increase as the foams are located more remotely (i.e., lower in the absorbent product) from the user.)

3. Resistance to Compression Deflection

An important mechanical feature of the foams of the present invention are their strength as determined by resistance to compression deflection (RTCD). The RTCD exhibited by the foams herein is a function of the polymer modulus, as well as the density and structure of the foam network. The polymer modulus is, in turn, determined by a) the polymer composition; b) the conditions under which the foam was polymerized (for example, the completeness of polymerization obtained, specifically with respect to crosslinking); and c) the extent to which the polymer is plasticized by residual materials, e.g., emulsifiers, left in the foam structure after processing.

To be useful as absorbent members in catamenials products, as well as other absorbent articles, the foams of the present invention must be suitably resistant to deformation or compression by forces encountered when such absorbent members are engaged in the absorption and retention of fluids. The RTCD exhibited by the polymeric foams of the present invention can be quantified by determining the amount of strain produced in a sample of saturated foam held under a certain confining pressure for a specified period of time. The method for carrying out this particular type of test is described hereafter in the TEST METHODS section. Foams useful as absorbents members for catamenial products are those which exhibit a RTCD such that a confining pressure of 0.74 psi (5.1 kPa) produces a strain of typically from about 5 to about 95% compression of the foam structure. Preferably the strain produced under such conditions will be in the range from about 10 to about 85%, most preferably from about 15 to about 80%.

4. Free Absorbent Capacity

Another important property of absorbent foams according to the present invention is their free absorbent capacity. For absorbent members useful in catamenial products, free absorbent capacity is the total amount of test fluid (i.e., synthetic urine) that a given foam sample will absorb at equilibrium into its cellular structure per unit mass of solid material in the sample. The foams that are especially useful as absorbent members in catamenial products will at least meet a minimum free absorbent capacity. The free absorbent capacity of the foams of the present invention can be determined using the procedure described in the TEST METHODS section of U.S. Pat. No. 5,387,207 (Dyer et al.) issued Feb. 7, 1995. To be especially useful as absorbent members for catamenial products, the foams of the present invention should have a free capacity of from about 20 to about 125 g/g, preferably from about 40 to about 70 g/g, and most preferably about 50 g/g, of synthetic urine per gram of dry foam.

C. Other Important Properties of Polymeric Foam

1. Cell and Hole Sizes

A feature that can be useful in defining preferred polymeric foams is cell size. Foam cells, and especially cells that are formed by polymerizing a monomer-containing oil phase that surrounds relatively monomer-free water-phase droplets, will frequently be substantially spherical in shape. The size or "diameter" of such spherical cells is a commonly used parameter for characterizing foams in general. Since cells in a given sample of polymeric foam will not necessarily be of approximately the same size, an average cell size, i.e., number average cell diameter, will often be specified.

Cell size is a foam parameter that can impact a number of important mechanical and performance features of the absorbent foams according to the present invention. Since cell size contributes to capillary suction specific surface area that, together with foam hydrophilicity, determines the capillarity of the foam, cell size is a foam structure parameter that can directly affect the fluid wicking properties of absorbent foams, as well as the capillary pressure that is developed within the foam structure.

Figure 3:
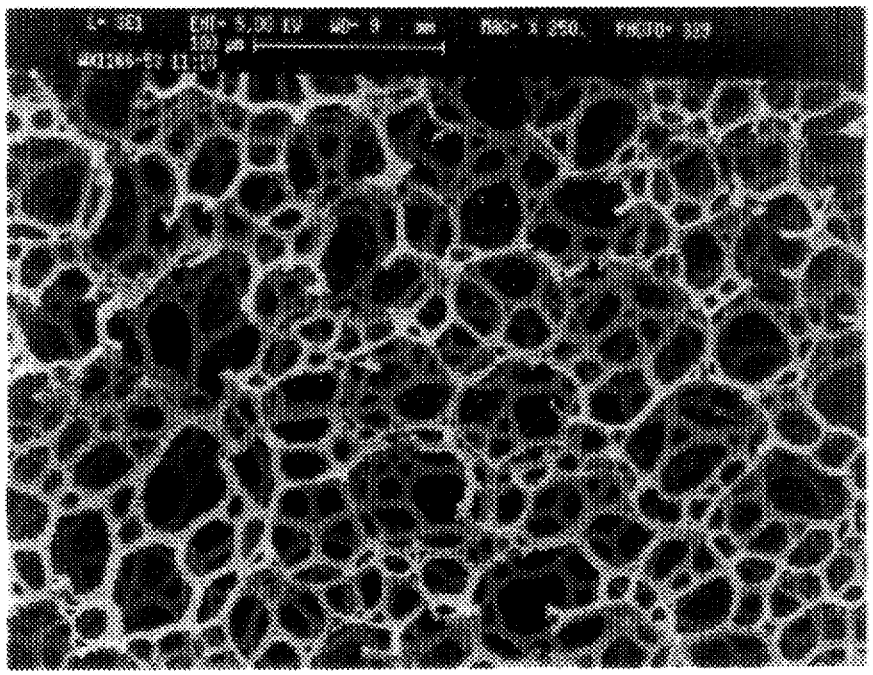
FIG. 3 of the drawings is a photomicrograph (250 X magnification) of a section of a representative absorbent polymeric foam according to the present invention made from HIPE having a 50:1 water-to-oil weight ratio and poured at 74° C., and where the monomer component consisted of a 5:21:14:60 weight ratio of styrene (STY) :ethyl styrene (EtS):divinyl benzene (DVB):2-ethylhexyl acrylate (EHA), and where 5.5% (by weight of the oil phase) of diglycerol monooleate (DGMO) and 1% of ditallow dimethyl ammonium methylsulfate emulsifiers are used.
Figure 4:
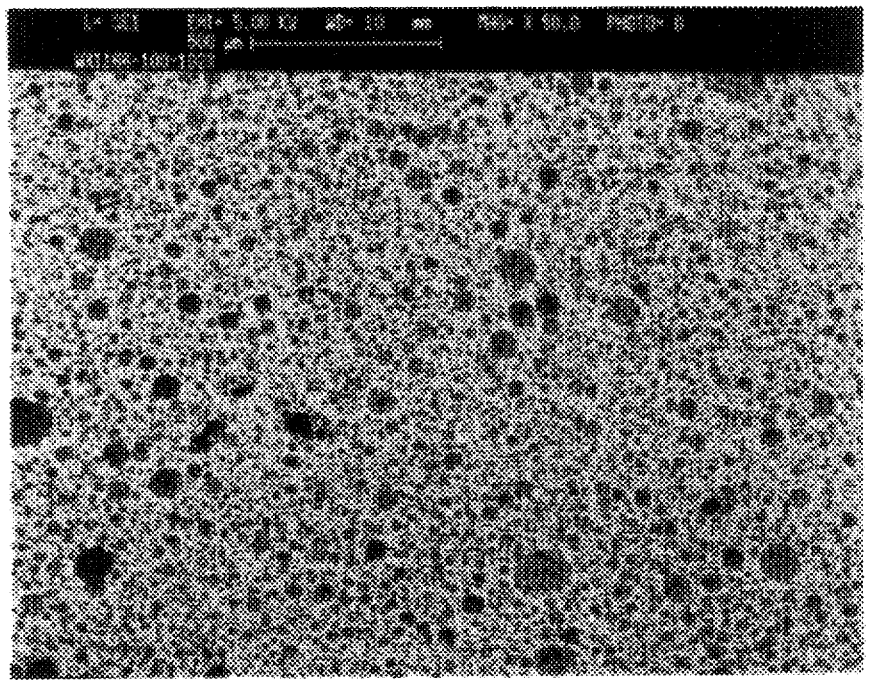
FIG. 4 is a photomicrograph (50 X magnification) of a section of a representative polymeric foam that is useful as the optional barrier layer beneath absorbent foam material(s) of the present invention. The foam is made from a HIPE having a 62.4:1 water-to-oil weight ratio and poured at 156° F. and 1300 RPM, where the monomer component consisted of a 19:14:55:12 weight ratio of ethyl styrene (EtS):divinyl benzene (DVB):2-ethylhexyl acrylate (EHA): 1,6-hexanedioldiacrylate (HDDA), and where 8% (by weight of the oil phase) of sorbitan myristate and 1% of ditallow dimethyl ammonium methyl sulfate emulsifiers are used.
Figure 5:
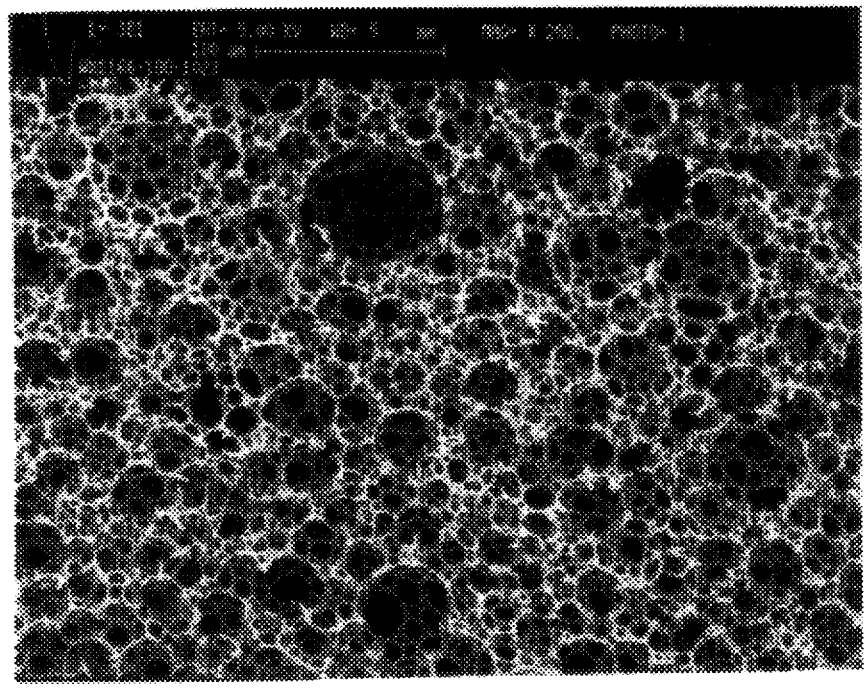
FIG. 5 is a photomicrograph of the foam shown in FIG. 4, but at 250 X magnification.
Figure 6:
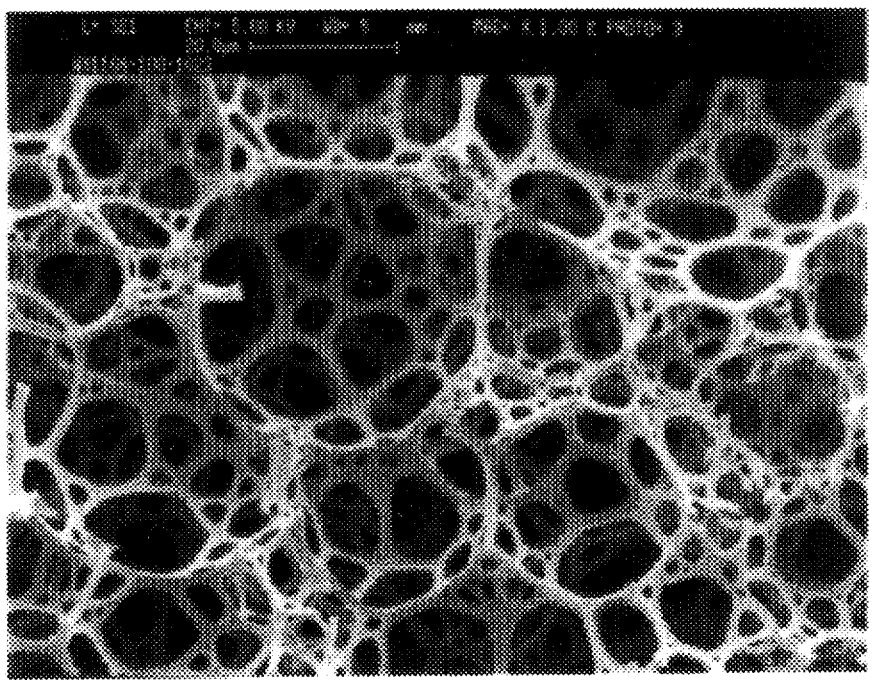
FIG. 6 is a photomicrograph of the foam shown in FIG. 4, but at 1000 X magnification.

A number of techniques are available for determining the average cell size of foams. The most useful technique for determining cell size in foams involves a simple measurement based on the scanning electron photomicrograph of a foam sample. FIG. 3, for example, shows a typical HIPE foam structure according to the present invention. Superimposed on the photomicrograph is a scale representing a dimension of 20 µm. Such a scale can be used to determine average cell size via visual inspection or an image analysis procedure.

The cell size measurements given herein are based on the number average cell size of the foam. The foams useful as absorbent members for catamenial products according to the present invention will preferably have a number average cell size of from about 20 to about 180 µm, and typically from about 35 to about 130 µm.

Another feature useful in defining these preferred foams is hole size. The holes are the openings between adjacent cells that maintain fluid communication between these cells. The foams of the present invention have hole sizes sufficiently large to allow passage of the insoluble components of blood, especially the red blood cells, to avoid blockage of these fluid passages.

The preferred technique for determining hole size is image analysis based on scanning electron micrographs of the foams as discussed above and shown in FIG. 3. The hole size measurements given herein are based on the number average hole size of the foam. The foams useful as absorbent members for catamenial products according to the present invention will preferably have a number average hole size of from about 4 to about 30 µm, and preferably from about 10 to about 28 µm. While foams having hole sizes larger than about 30 µm will allow passage of blood cells, they will not have the fine microstructure necessary to provide the fluid capillary absorbent pressure of the foams of the present invention.

2. Foam Density

"Foam density" (i.e., in grams of foam per cubic centimeter of foam volume in air) is specified herein on a dry basis. The density of the foam, like capillary suction specific surface area, can influence a number of performance and mechanical characteristics such as the RTCD of absorbent foams. Importantly also, the density of the foam controls the absorbent capacity of such foams in units of g/g. This influences the cost effectiveness and utility of such foams as absorbent members for catamenial products.

Any suitable gravimetric procedure that will provide a determination of mass of solid foam material per unit volume of foam structure can be used to measure foam density. An ASTM gravimetric procedure described more fully in the TEST METHODS section of U.S. Pat. No. 5,387,207 (Dyer et al.) issued Feb. 7, 1995 is the preferred method that can be employed for density determinations. Polymeric foams of the present invention useful as absorbent members for catamenial products have dry basis density values in the range of from about 0.008 to about 0.05 g/cc, preferably from about 0.014 to about 0.024 g/cc, and most preferably about 0.02 g/cc.

3. Horizontal Gravimetric Wicking

One of the primary benefits of the foams of the present invention is their ability to retain absorbed blood and blood-based fluids, even when subjected to compressive load. A foam of insufficient strength (RTCD) will express excess fluid readily during use. Under mechanical pressure from the wearer of the catamenial product, this mobile fluid can be pumped out of the absorbent core and upwards through the topsheet. As a result, the topsheet becomes "rewetted" with this pumped fluid such that there is not adequate topsheet dryness.

The ability of the foams of the present invention to minimize rewet can be correlated to their ability to retain absorbed fluids. The ability of these foams to retain absorbed fluids can be measured by Horizontal Gravimetric Wicking (HGW), the procedure for which is described hereafter in the Test Methods section. For the purposes of the present invention this HGW measurement is expressed as the percentage of the Retained Uptake of AMF, relative to the Initial Uptake of AMF, or "% Retained/Initial Uptake of AMF." The foams of the present invention typically have a % Retained/Initial Uptake of AMF of at least about 50%, and preferably at least about 65%.

II. Polymeric Foam Barrier Layer

As indicated herein, many users of catamenial products prefer relatively thick pads. With such pads, inexpensive filler materials, which may possess pore absorbent/wet integrity properties, may be preferred. However, when such materials are used, the resulting absorbent products may suffer from an aesthetic and/or performance standpoint. Because the absorbent polymeric foams of the present invention provide high fluid acquisition/storage capabilities, such filler materials can be used without compromising performance. For example, keeping the filler material (e.g., airfelt) relatively free from liquid results in less bunching and/or roping in use. This results in better core and product integrity in use. To further facilitate maintanence of a relatively dry filler layer, in a preferred embodiment of the present invention a polymeric foam material (referred to herein as a "barrier layer") is used as the lowest layer of the absorbent core material. This optional barrier layer is useful in that it significantly limits passage of blood/fluid into optional materials (e.g., fillers such as air felt) below the absorbent foam core material.

To prevent fluid flow into filler material located immediately above the backsheet, the barrier layer preferably has an average cell size from about 15 to about 50 µm, preferably from about 25 to about 35 µm; and an average hole size from about 4 to about 9 µm, preferably from about 5 to about 7 µm. These relatively small cell sizes tend to filter out the red blood cells in blood and blood based fluids, thus preventing passage of this color into lower layers of filler material. The fluid which is admitted into the barrier layers is further retained by the relatively high fluid capillary pressure associated with such structures. Thus, when the absorbent foam core is placed on top of, e.g., an air laid fibrous core, the barrier layer serves to prevent contamination of the air laid core with fluid which would cause the air laid core to change its dimensions and lose its integrity and/or be stained with the red color.

While the primary function of the barrier layer is to inhibit fluid (especially blood) flow to lower product layers, this foam material preferably possesses the ability to move fluid away from the wearer. Thus, it is preferred that barrier layer have a higher capillary specific suction surface area than the absorbent foam layers located above (closer to the user) it. For example, where two foam layers of the present invention having capillary specific surface areas as described in section I-b herein, it is preferred that the barrier layer will have a capillary suction specific surface area of from about 0.040 to about 0.080 m²/cc. In this way, the foam layers of the absorbent core have successively higher fluid capillary pressure providing drainage away from the wearers body. The barrier layer's ability to acquire and store fluid may allow for enhanced fluid retention by the article under circumstances where the absorbent foam materials (discussed above) have reached their capacity or where fluid is "squeezed out" of the foam layers overlying the barrier layer.

III. Preparation of Polymeric Foams From HIPE

A. In General

Polymeric foams according to the present invention can be prepared by polymerization of certain water-in-oil emulsions having a relatively high ratio of water phase to oil phase commonly known in the art as "HIPEs." Polymeric foam materials which result from the polymerization of such emulsions are referred to herein as "HIPE foams."

The relative amounts of the water and oil phases used to form the HIPEs are, among many other parameters, important in determining the structural, mechanical and performance properties of the resulting polymeric foams. In particular, the ratio of water to oil (W:O) in the HIPEs varies inversely with ultimate foam density according to the equation:

Density=1/(W:O ratio+1).

This can influence the cell size and capillary specific surface area of the foam and dimensions of the struts that form the foam. The HIPEs used to prepare the foams of the present invention will generally have a volume to weight ratio of water phase to oil phase in the range of from about 20:1 to about 125:1, more preferably from about 40:1 to about 70:1, most preferably about 50:1.

1. Oil Phase Components

The continuous oil phase of the HIPE comprises monomers that are polymerized to form the solid foam structure. This monomer component is formulated to be capable of forming a copolymer having a Tg of about 50° C. or lower, and typically from about 15° to about 30° C. (The method for determining Tg by Dynamic Mechanical Analysis (DMA) is described hereafter in the TEST METHODS section.) This monomer component includes: (a) at least one monofunctional monomer capable of forming an atactic amorphous polymer having a Tg of about 35° C. or lower (see Brandup, J.; Immergut, E. H. "Polymer Handbook", 2nd ed., Wiley-Interscience New York, N.Y., 1975, III-139.); (b) at least one monofunctional comonomer to improve the toughness or tear resistance of the foam; (c) a first polyfunctional crosslinking agent; and (d) optionally a second polyfunctional crosslinking agent. Selection of particular types and amounts of monofunctional monomer(s), comonomer(s) and polyfunctional crosslinking agent(s) can be important to the realization of absorbent HIPE foams having the desired combination of structure, mechanical, and fluid handling properties.

The monomer component comprises one or more monomers that tend to impart rubber-like properties to the resulting polymeric foam structure. Such monomers can produce high molecular weight (greater than 10,000) atactic amorphous polymers having Tg's of about 35° C. or lower. Monomers of this type include, for example, the ($C_4$–$C_{14}$) alkyl acrylates such as butyl acrylate, hexyl acrylate, octyl acrylate, 2-ethylhexyl acrylate, nonyl acrylate, decyl acrylate, dodecyl (lauryl) acrylate, isodecyl acrylate tetradecyl acrylate, aryl and alkaryl acrylates such as benzyl acrylate, and nonylphenyl acrylate, the ($C_6$–$C_{16}$) alkyl methacrylates such as hexyl methacrylate, octyl methacrylate, nonyl methacrylate, decyl methacrylate, isodecyl methacrylate, dodecyl (lauryl) methacrylate, tetradecyl methacrylate; acrylamides such as N-octadecyl acrylamide; ($C_4$–$C_{12}$) alkyl styrenes such as p-n-octylstyrene, isoprene, butadiene, and combinations of such monomers. Of these monomers, isodecyl acrylate, dodecyl acrylate and 2-ethylhexyl acrylate are the most preferred. The monofunctional monomer(s) will generally comprise 45 to about 70%, more preferably from about 50 to about 65%, by weight of the monomer component.

The monomer component utilized in the oil phase of the HIPEs also comprises one or more monofunctional comonomers capable of imparting toughness about equivalent to that provided by styrene to the resulting polymeric foam structure. Tougher polymers exhibit the ability to deform substantially without failure. These monofunctional comonomer types can include styrene-based comonomers (e.g., styrene and ethyl styrene) or other monomer types such as methyl methacrylate where the related homopolymer is well known as exemplifying toughness. The preferred monofunctional comonomer of this type is a styrene-based monomer with styrene and ethyl styrene being the most preferred monomers of this kind. The monofunctional "toughening" comonomer will normally comprise from about 10 to about 40%, preferably from about 15% to about 40%, most preferably from about 18% about 28%, by weight of the monomer component.

In certain cases, the "toughening" comonomer can also impart the desired rubber-like properties to the resultant polymer. The ($C_4$–$C_{12}$) alkyl styrenes, and in particular p-n-octylstyrene, are examples of such comonomers. For such comonomers, the amount that can be included in the monomer component will be that of the typical monomer and comonomer combined.

The monomer component also contains a first (and optionally second) polyfunctional crosslinking agent. As with the monofunctional monomers and comonomers, selection of the particular type and amount of crosslinking agents is very important to the eventual realization of preferred polymeric foams having the desired combination of structural, mechanical, and fluid-handling properties.

The first polyfunctional crosslinking agent can be selected from a wide variety of polyvinyl aromatic and related polyvinyl materials such as divinylbenzenes, trivinylbenzenes, divinyltoluenes, divinylxylenes, divinylnaphthalenes divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinylsulfone, and mixtures thereof. Divinyl benzene is typically available as a mixture with ethyl styrene in proportions of about 55:45. These proportions can be modified so as to enrich the oil phase with one or the other component. Generally, it is advantageous to enrich the mixture with the ethyl styrene component while simultaneously reducing the amount of styrene in the monomer blend. The preferred ratio of divinyl benzene to ethyl styrene is between from about 30:70 and 55:45, most preferably from between about 35:65 to about 45:55. The inclusion of higher levels of ethyl styrene imparts the required toughness without increasing the Tg of the resulting copolymer to the degree that styrene does. This first crosslinking agent can generally be included in the oil phase of the HIPE in an amount of from about 8% to about 22%, more preferably from about 10% to about 18%, most preferably from about 12% to about 16%, by weight of the monomer component.

The optional second crosslinking agent can be selected from polyfunctional acrylates and methacrylates, acrylamides and methacrylamides, and mixtures thereof. These include di-, tri-, and tetra-acrylates, as well as di-, tri-, and tetra- methacrylates; di-, tri-, and tetra-acrylamides, as well as di-, tri-, and tetra- methacrylamides; and mixtures of these crosslinking agents. Suitable acrylate and methacrylate crosslinking agents can be derived from diols, triols and tetraols that include 1,10-decanediol, 1,8-octanediol, 1,6-hexanediol, 1,4-butanediol, 1,3-butanediol, 1,4-but-2-enediol, ethylene glycol, diethylene glycol, trimethylolpropane, pentaerythritol, hydroquinone, catechol, resorcinol, triethylene glycol, polyethylene glycol, sorbitol, and the like. (The acrylamide and methacrylamide crosslinking agents can be derived from the equivalent diamines, triamines and tetramines). The preferred diols have at least 2, more preferably at least 4, most preferably 6, carbon atoms. This second cross-linking agent can generally be included in the oil phase of the HIPE in an amount of from 0 to about 15%, preferably from 0 to about 13%, by weight of the monomer component.

Without being bound by theory, it is believed this second crosslinking agent generates a more homogeneously crosslinked structure that develops strength more efficiently than using either the first or the second crosslinker alone at comparable levels. The second crosslinker also has the effect of broadening the glass-to-rubber transition region. This broader transition region can be tailored to meet specific strength and resilience requirements at in-use temperatures by controlling the relative amount of the two crosslinker types employed. Thus, a foam containing only the first type of crosslinker will exhibit a relatively narrow transition region. Increasing the amount of the second crosslinker serves to broaden the transition region, even if the actual transition temperature itself has not changed.

The major portion of the oil phase of the HIPEs will comprise the aforementioned monomers, comonomers and crosslinking agents. It is essential that these monomers, comonomers and crosslinking agents be substantially water-insoluble so that they are primarily soluble in the oil phase and not the water phase. Use of such substantially water-insoluble monomers ensures that HIPEs of appropriate characteristics and stability will be realized. It is, of course, highly preferred that these monomers, comonomers and crosslinking agents be of the type such that the resulting polymeric foam is suitably non-toxic and appropriately chemically stable. These monomers, comonomers and crosslinking agents should preferably have little or no toxicity if present at very low residual concentrations during post-polymerization foam processing and/or use.

Another essential component of the oil phase is an emulsifier component that permits the formation of stable HIPEs. This emulsifier component comprises a primary emulsifier and optionally a secondary emulsifier. Especially when used alone, these primary emulsifer typically comprise at least about 40%, preferably at least about 70%, emulsifying components selected from diglycerol monoesters of linear unsaturated $C_{16}$–$C_{22}$ fatty acids, diglycerol monoesters of branched $C_{16}$–$C_{24}$ fatty acids, diglycerol monoaliphatic ethers of branched $C_{16}$–$C_{24}$ alcohols, diglycerol monoaliphatic ethers of linear unsaturated $C_{16}$–$C_{22}$ alcohols, diglycerol monoaliphatic ethers of linear saturated $C_{12}$–$C_{14}$ alcohols, sorbitan monoesters of linear unsaturated $C_{16}$–$C_{22}$ fatty acids, sorbitan monoesters of branched $C_{16}$–$C_{24}$ fatty acids, and mixtures thereof. Preferred primary emulsifiers include diglycerol monooleate (e.g., preferably greater than about 40%, more preferably greater than about 50%, most preferably greater than about 70% diglycerol monooleate), sorbitan monooleate (e.g., preferably greater than about 40%, more preferably greater than about 50%, most preferably greater than about 70% sorbitan monooleate), sorbitan monopalmitate, and diglycerol monoisostearate (e.g., preferably greater than about 40%, more preferably greater than about 50%, most preferably greater than about 70% diglycerol monoisostearate).

Diglycerol monoesters of linear unsaturated and branched fatty acids useful as emulsifiers in the present invention can be prepared by esterifing diglycerol with fatty acids, using procedures well known in the art. See, for example, the method for preparing polyglycerol esters disclosed in U.S. Pat. No. 5,387,207 (Dyer et al.) issued Feb. 7, 1995. Diglycerol can be obtained commercially or can be separated from polyglycerols that are high in diglycerol. Linear, branched, and unsaturated fatty acids can be obtained commercially. The mixed ester product of the esterification reaction can be fractionally distilled under vacuum one or more times to yield distillation fractions that are high in diglycerol monoesters. For example, a A CMS-15A (C.V.C.

Products Inc.; Rochester, N.Y.) continuous 14 inch centrifugal molecular still can be used for fractional distillation. Typically, the polyglycerol ester feedstock, while being heated, is first metered through a degasser unit and then to the heated evaporator cone of the still, where the vacuum distillation takes place. Distillate is collected on the bell jar surface, which can be heated to facilitate distillate removal. Distillate and residue are continuously removed by transfer pumps. The fatty acid composition of the resultant mixed ester product can be determined using high resolution gas chromatography. See U.S. Pat. No. 5,387,207 (Dyer et al.) issued Feb. 7, 1995. Polyglycerol and polyglycerol ester distribution of the resultant mixed ester product can be determined by capillary supercritical chromatography.

Linear saturated, linear unsaturated, or branched diglycerol monoaliphatic ethers can also be prepared and their composition determined using procedures well known in the art. See also copending U.S. application Ser. No. 08/514,346 (Stephen A. Goldman et al), filed Aug. 9, 1995 (P&G Case No. 5540C), which is incorporated by reference.

Sorbitan monoesters of linear unsaturated and branched fatty acids can be obtained commercially or prepared using methods known in the art. See, for example, U.S. Pat. No. 4,103,047 (Zaki et al), issued Jul. 25, 1978 (herein incorporated by reference), especially column 4, line 32 to column 5, line 13. The mixed sorbitan ester product can be fractionally vacuum distilled to yield compositions that are high in sorbitan monoesters. Sorbitan ester compositions can be determined by methods well known in the art such as small molecule gel permeation chromatography. See copending U.S. application Ser. No. 08/514,346 (P&G Case 5540C), which describes the use of this method for polyglycerol aliphatic ethers.

When these primary emulsifiers are used in combination with certain secondary emulsifiers, the primary emulsifier can comprise lower levels of these emulsifying components, i.e., as low as about 20% of these emulsifying components. These secondary emulsifiers are at least cosoluble with the primary emulsifier in the oil phase. Suitable secondary emulsifiers can be cationic types, including the long chain $C_{12}-C_{22}$ dialiphatic, short chain $C_1-C_4$ dialiphatic quaternary ammonium salts such as ditallow dimethyl ammonium chloride, bistridecyl dimethyl ammonium chloride, and ditallow dimethyl ammonium methylsulfate, the long chain $C_{12}-C_{22}$ dialkoyl(alkenoyl)-2-hydroxyethyl, short chain $C_1-C_4$ dialiphatic quaternary ammonium salts such as ditallowoyl-2-hydroxyethyl dimethyl ammonium chloride, the long chain $C_{12}-C_{22}$ dialiphatic imidazolinium quaternary ammonium salts such as methyl-1-tallow amido ethyl-2-tallow imidazolinium methylsulfate and methyl-1-oleyl amido ethyl-2-oleyl imidazolinium methylsulfate, the short chain $C_1-C_4$ dialiphatic, long chain $C_{12}-C_{22}$ monoaliphatic benzyl quaternary ammonium salts such as dimethyl stearyl benzyl ammonium chloride; anionic typos including the $C_6-C_{18}$ dialiphatic esters of sodium sulfosuccinic acid such as the dioctyl ester of sodium sulfosuccinic acid and the bistridecyl ester of sodium sulfosuccinic acid; and mixtures of these secondary emulsifiers. These secondary emulsifiers can be obtained commercially or prepared using methods known in the art. The preferred secondary emulsifiers are ditallow dimethyl ammonium methyl sulfate and ditallow dimethyl ammonium methyl chloride. When these optional secondary emulsifiers are included in the emulsifier component, it is typically at a weight ratio of primary to secondary emulsifier of from about 50:1 to about 1:4, preferably from about 30:1 to about 2:1.

The oil phase used to form the HIPEs comprises from about 85 to about 98% by weight monomer component and from about 2 to about 15% by weight emulsifier component. Preferably, the oil phase will comprise from about 90 to about 97% by weight monomer component and from about 3 to about 10% by weight emulsifier component. The oil phase also can contain other optional components. One such optional component is an oil soluble polymerization initiator of the general type well known to those skilled in the art, such as described in U.S. Pat. No. 5,290,820 (Bass et al), issued Mar. 1, 1994, which is incorporated by reference. Another preferred optional component is an antioxidant such as a Hindered Amide Light Stabilizer (HALS) and Hindered Phenolic Stabilizers (HPS) or any other antioxidant compatible with the initiator system to be employed. Other optional components include plasticizers, fillers, colorants, chain transfer agents, dissolved polymers, and the like.

2. Water Phase Components

The discontinuous water internal phase of the HIPE is generally an aqueous solution containing one or more dissolved components. One essential dissolved component of the water phase is a water-soluble electrolyte. The dissolved electrolyte minimizes the tendency of monomers, comonomers, and crosslinkers that are primarily oil soluble to also dissolve in the water phase. This, in turn, is believed to minimize the extent to which polymeric material fills the cell windows at the oil/water interfaces formed by the water phase droplets during polymerization. Thus, the presence of electrolyte and the resulting ionic strength of the water phase is believed to determine whether and to what degree the resulting preferred polymeric foams can be open-celled.

Any electrolyte capable of imparting ionic strength to the water phase can be used. Preferred electrolytes are mono-, di-, or trivalent inorganic salts such as the water-soluble halides, e.g., chlorides, nitrates and sulfates of alkali metals and alkaline earth metals. Examples include sodium chloride, calcium chloride, sodium sulfate and magnesium sulfate. Calcium chloride is the most preferred for use in the present invention. Generally the electrolyte will be utilized in the water phase of the HIPEs in a concentration in the range of from about 0.2 to about 20% by weight of the water phase. More preferably, the electrolyte will comprise from about 1 to about 10% by weight of the water phase.

The HIPEs will also typically contain a polymerization initiator. Such an initiator component is generally added to the water phase of the HIPEs and can be any conventional water-soluble free radical initiator. These include peroxygen compounds such as sodium, potassium and ammonium persulfates, hydrogen peroxide, sodium peracetate, sodium percarbonate and the like. Conventional redox initiator systems can also be used. Such systems are formed by combining the foregoing peroxygen compounds with reducing agents such as sodium bisulfite, L-ascorbic acid or ferrous salts.

The initiator can be present at up to about 20 mole percent based on the total moles of polymerizable monomers present in the oil phase. More preferably, the initiator is present in an amount of from about 0.001 to about 10 mole percent based on the total moles of polymerizable monomers in the oil phase.

3. Hydrophilizing Surfactants

The polymer forming the HIPE foam structure will preferably be substantially free of polar functional groups. This means the polymeric foam will be relatively hydrophobic in character. To be useful as absorbents for blood and blood-based fluids such as menses, these foams generally require further treatment to render the foam relatively more hydrophilic. Hydrophilization of the foam, if necessary, can generally be accomplished by treating the HIPE foam with a hydrophilizing surfactant in a manner described more fully hereafter.

These hydrophilizing surfactants can be any material that enhances the water wettability of the polymeric foam surface. Suitable surfactants should be non-toxic and non-irritating to mucus membranes. It should be soluble or dispersible in warm water. Preferably, the hydrophilizing surfactant is a liquid at temperatures near ambient for ease of incorporation during the foam making process. Suitable surfactants include ethoxylates of $C_{11}$–$C_{15}$ alcohols, marketed by Shell Chemical Co., in particular NEODOL 25-12 (condensation product of $C_{12}$–$C_{15}$ linear alcohols with 12 moles of ethylene oxide), NEODOL 23-6.5T (condensation product of $C_{12}$–$C_{13}$ linear alcohols with 6.5 moles of ethylene oxide that has been distilled (topped) to remove certain impurities), and NEODOL 23-3 (condensation product of $C_{12}$–$C_{13}$ linear alcohols with 3 moles of ethylene oxide); ethoxylates of $C_{11}$–$C_{15}$ fatty acids sold under the PEGOSPERSE designation by Stepan Chemical Corp., Northfield, Ill.; condensation products of ethylene oxide and/or propylene oxide having molecular weights greater than about 2000, and condensation products of propylene oxide and propylene glycol sold under the PLURONIC designation by BASF Parisspany, N.J.; modified oxyethylated straight chain alcohols sold under the Plurafac designation by BASF, Corp., Parsippany, N.J.; sulfated alcohol ethoxylates and alkyl ether sulfates such as those sold by Harcos Chemicals, Kansas, Kans., branched and linear alkyl aryl ethoxylates such as Triton X-60, Triton X-100, Triton N-57, and the like marketed by Union Carbide, Inc. Danbury, Conn., silicone-glycol copolymers sold under the SILWET designation by OSI Specialties, Danbury, Conn., as well as mixtures of these surfactants. Particularly preferred surfactants are PEGOSPERSE 200 ML, an ethoxylate of lauric acid having an average of 4.5 ethoxy units.

These hydrophilizing surfactants can be dissolved or dispersed in a hydrophilizing solution that is applied to the HIPE foam surface. In this manner, hydrophilizing surfactants can be adsorbed by the preferred HIPE foams in amounts suitable for rendering the surfaces thereof substantially hydrophilic, but without substantially impairing the desired flexibility and compression deflection characteristics of the foam. In preferred foams, the hydrophilizing surfactant is incorporated such that residual amounts of the surfactant that remain in the foam structure are typically in the range from about 0.05% to about 5%, preferably from about 0.5 to about 1%, by weight of the foam.

B. Processing Conditions for Obtaining HIPE Foams

Foam preparation typically involves the steps of: 1) forming a stable high internal phase emulsion (HIPE); 2) polymerizing/curing this stable emulsion under conditions suitable for forming a solid polymeric foam structure; 3) slicing or otherwise cutting the water-filled polymeric foam and then washing the sliced or cut foam to remove the original residual water phase, and especially the residual hydratable salts, from the polymeric foam structure; 4) treating the polymeric foam structure with a hydrophilizing surfactant; and thereafter dewatering this polymeric foam structure.

1. Formation of HIPE

The HIPE is formed by combining the oil and water phase components in the previously specified weight ratios. The oil phase will typically contain the requisite monomers, comonomers, crosslinkers, and emulsifiers, as well as optional components such as solvents and polymerization initiators. The water phase will typically contain electrolytes, as well as optional components such as water-soluble emulsifiers, and/or polymerization initiators.

The HIPE can be formed from the combined oil and water phases by subjecting these combined phases to shear agitation. Shear agitation is generally applied to the extent and for a time period necessary to form a stable emulsion. Such a process can be conducted in either batchwise or continuous fashion and is generally carried out under conditions suitable for forming an emulsion where the water phase droplets are dispersed to such an extent that the resulting polymeric foam will have the requisite cell size and other structural characteristics. Suitable mixing or agitation devices are those that are capable of forming an emulsion under conditions of low shear mixing. Emulsification of the oil and water phase combination will frequently involve the use of a mixing or agitation device such as a pin impeller.

One preferred method of forming such HIPEs involves a continuous process that combines and emulsifies the requisite oil and water phases. In such a process, a liquid stream comprising the oil phase is formed. Concurrently, a liquid stream comprising the water phase is also formed. The two streams are then combined in a suitable mixing chamber or zone such that the requisite water to oil phase weight ratios previously specified are achieved.

In the mixing chamber or zone, the combined streams are generally subjected to shear agitation provided, for example, by a pin impeller of suitable configuration and dimensions. Shear will typically be applied to the combined oil/water phase stream at at a rate of about 4000 sec$^{-1}$ or less, preferably about 3000 sec$^{-1}$ or less. Once formed, the stable liquid HIPE can then be withdrawn from the mixing chamber or zone. This preferred method for forming HIPEs via a continuous process is described in greater detail in U.S. Pat. No. 5,149,720 (DesMarais et al), issued Sep. 22, 1992, which is incorporated by reference. See also copending U.S. application Ser. No. 08/370,694 (Thomas A. DesMarais), filed Jan. 10, 1995 (P&G Case No. 5543) (herein incorporated by reference), which describes an improved continuous process having a recirculation loop for the HIPE.

The degree of shear applied and/or the water to oil phase ratio during HIPE formation need not be constant throughout. For example, HIPE making can be carried out under "pulsed" conditions or varied rhythmically. This is especially useful when the HIPE is collected in a rotating cylindrical container as successive layers to form foams having heterogeneous structures. Pulsed conditions can produce HIPEs comprising regions of larger and smaller celled foam in an alternating sequence. After curing and slicing as described hereafter, this can provide foams having the ability to control the direction of movement of the absorbed fluid within the foam. For example, fluid movement can be induced to occur along the line of pour of the foam.

One particular advantage of the more robust emulsifier systems used in these HIPEs is that the mixing conditions during HIPE formation and pouring can be carried out at more elevated temperatures of about 50° C. or higher, preferably 60° C. or higher. Typically, the HIPE can be formed at a temperature of from about 60° to about 99° C., more typically from about 65° to about 85° C.

2. Polymerization/Curing of the HIPE

The HIPE formed will generally be collected or poured into a suitable reaction vessel, container or region to be polymerized or cured. In one embodiment, the reaction vessel comprises a tub constructed of polyethylene from which the eventually polymerized/cured solid foam material can be easily removed for further processing after polymerization/curing has been carried out to the extent desired. It is usually preferred that the temperature at which the HIPE is poured into the vessel be approximately the same as the polymerization/curing temperature.

Suitable polymerization/curing conditions will vary depending upon the monomer and other makeup of the oil and water phases of the emulsion (especially the emulsifier systems used), and the type and amounts of polymerization initiators used. Frequently, however, suitable polymerization/curing conditions will involve maintaining the HIPE at elevated temperatures above about 50° C., more preferably above about 65° C., and most preferably above about 80° C., for a time period ranging from about 2 to about 64 hours, more preferably from about 2 to about 48 hours. The HIPE can also be cured in stages such as described in U.S. Pat. No. 5,189,070 (Brownscombe et al), issued Feb. 23, 1993, which is herein incorporated by reference.

A porous water-filled open-celled HIPE foam is typically obtained after polymerization/curing in a reaction vessel, such as a tub. This polymerized HIPE foam is typically cut or sliced into a sheet-like form. Sheets of polymerized HIPE foam are easier to process during subsequent treating/ washing and dewatering steps, as well as to prepare the HIPE foam for use in absorbent articles. The polymerized HIPE foam is typically cut/sliced to provide a cut thickness in the range of from about 0.08 to about 2.5 cm, preferably from about 0.15 and about 2 cm. The polymerized HIPE foam can also be cubed or sliced into thin spaghetti-like sections or can be stamped into shapes such as a continuous tube (e.g., for use in tampons) at this point.

3. Slicing and Washing HIPE Foam

The solid polymerized HIPE foam formed will generally be filled with residual water phase material used to prepare the HIPE. This residual water phase material (generally an aqueous solution of electrolyte, residual emulsifier, and polymerization initiator) should be at least partially removed prior to further processing and use of the foam. Removal of this original water phase material will usually be carried out after slicing the foam into sheets of from about 0.15 to about 0.4 cm in thickness. These sheets are dewatered by compressing the foam structure to squeeze out residual liquid and/or by washing the foam structure with water or other aqueous washing solutions. Frequently several compressing and washing steps, e.g., from 2 to 4 cycles, will be used.

The removal of most of the residual electrolyte (i.e., hydratable salts) from the foam is particularly important. As noted previously, these hydratable salts are typically included during initial formation of the HIPE to minimize the tendency of monomers, comonomers, and crosslinkers that are primarily oil soluble to also dissolve in the water phase. However, after polymerization of the HIPE, the presence of these salts is unnecessary and can adversely affect the ability of the foam to absorb blood and blood-based fluids such as menses, especially as the concentration of these salts in the foam increases. Accordingly, it desirable to reduce the level of these hydratable salts in the foam as much as possible during this washing step. After washing, the foams of the present invention have less than about 2% of such residual hydratable salts. Preferably, the foams of the present invention have less than about 0.5% of such residual salts.

4. Treating with Hydrophilizing Surfactant and Foam Dewatering

After the original water phase material has been removed to the extent required, the HIPE foam is typically treated with an effective amount of a suitable hydrophilizing surfactant. Hydrophilizing surfactants that can be employed have been previously described and particularly include ethoxylates of $C_{11}-C_{15}$ fatty acids such as Pegosperse 200 ML, branched and linear alkyl aryl ethoxylates such as Triton X-100, and ethoxylates of $C_{11}-C_{15}$ aliphatic alcohols such as NEODOL 23-6.5T. Treatment of the HIPE foam with the hydrophilizing surfactant continues until the foam exhibits the desired degree of wettability.

After the HIPE foam has been hydrophilized, it will generally be dewatered. Dewatering can be achieved by compressing the foam (preferably in the z-direction) to squeeze out residual water, by subjecting the foam and the water therein to temperatures of from about 60° to about 200° C., or to microwave treatment, by vacuum dewatering or by a combination of compression and thermal drying/ microwave/vacuum dewatering techniques. The dewatering step will generally be carried out until the HIPE foam is ready for use and is as dry as practicable. Frequently such compression dewatered foams will have a water (moisture) content of from about 50 to about 500%, more preferably from about 50 to about 200%, by weight on a dry weight basis. Subsequently, the compressed foams can be thermally dried to a moisture content of about 40% or less, preferably in the range of from about 5 to about 15%, on a dry weight basis.

After the HIPE foam has been dewatered, it can be slitted in various patterns. These include patterns that conform to the shape of the catamenial product in which the slitted foam is used as an absorbent member. Slitting can be especially desirable when the foam is intended to confer superior fit in a catamenial pad such as a sanitary napkin.

IV. Use of Polymeric Foams in Catamenial Products

The polymeric foams of the present invention are useful in a variety of absorbent articles for absorbing blood and blood-based fluids.

A. Catamenial Products

The polymeric foams of the present invention are particularly useful as absorbent members in a variety of catamenial products such as catamenial pads. An embodiment of a catamenial pad or sanitary napkin 10 according to the present invention is shown in FIG. 1. As used herein, the term "sanitary napkin" refers to an absorbent article that is worn by females adjacent to the pudendal region, generally external to the urogenital region, and which is intended to absorb and contain menstrual fluids and other vaginal discharges from the wearer's body (e.g., blood, menses, and urine). Interlabial devices that reside partially within and partially external of the wearer's vestibule are also within the scope of the present invention. As used herein, the term "pudendal" refers to the externally visible female genitalia. It should be understood, however, that the present invention is also applicable to other feminine hygiene or catamenial pads such as pantiliners, or other catamenial products such as incontinence pads, tampons and the like.

The polymeric foams of the present invention are particularly useful in sheet form. This relates to ease of manufacture and shipping as well as for general utility in the product. The sheet or sheets used can be of any thickness desired according to the capacity required for the surface area available. Generally, the sheets will be from about 0.1 to about 1 cm in thickness. These sheets can be perforated or slit, either to further enhance the rate of fluid absorption by increasing the surface area of the foam exposed to the fluid or to increase the stretchability of the foam. Alternatively, these foams can be in the form of diced cubes, strands (e.g. spaghetti-like material), thin strips, and the like that can be assembled into absorbent cores of various shapes depending on the specific needs of the product.

Figure 2:
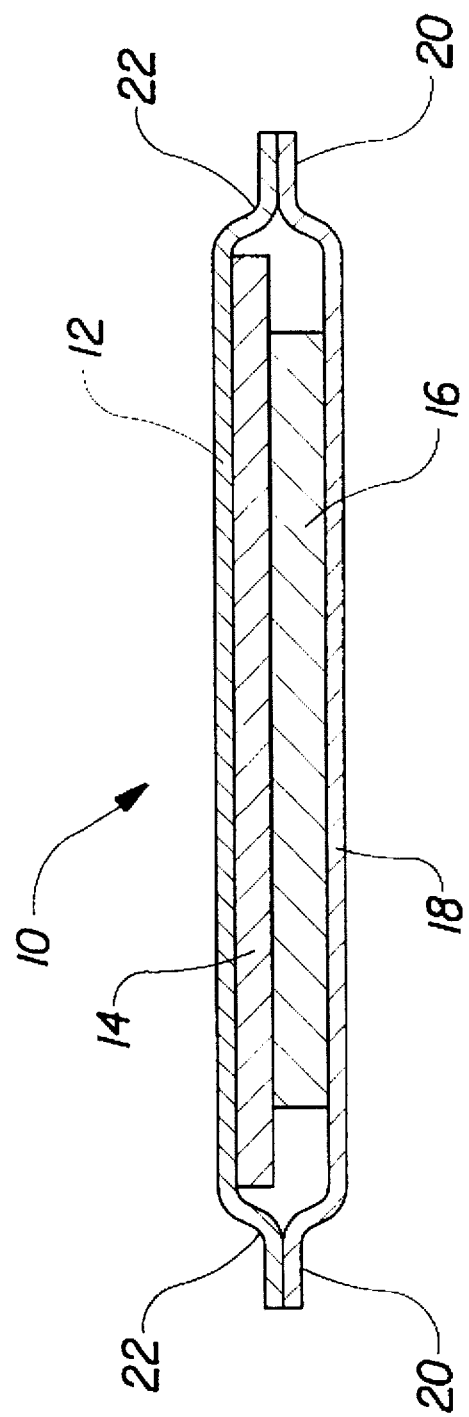
FIG. 2 of the drawings is a cross-sectional view take along line 2—2 of FIG. 2.

As particularly shown in FIG. 2, catamenial pad 10 is constructed of fluid pervious primary topsheet 12, an absorbent core consisting of an optional fluid acquisition layer 14 commonly referred to as a "secondary topsheet", a fluid storage absorbent member 16 made of one or more polymeric foams according to the present invention, and a fluid impervious backsheet 18. The fluid storage absorbent member 16 may also comprise a polymeric foam barrier layer of the present invention. The backsheet 18 and the topsheet 12 are positioned adjacent the garment surface and the body surface, respectively, of pad 10 and are preferably joined to each other. For example, the backsheet 18 and the topsheet 12 can be secured to each other by adhesive. Suitable adhesives tare manufactured by H. B. Fuller Company of St. Paul, Minn. under the designation HL-1258 or H-2031. Alternatively, topsheet 12 and backsheet can be joined to each other by heat bonding, pressure bonding, ultrasonic bonding, dynamic mechanical bonding, or any other suitable method for joining topsheets and backsheets known in the art.

A suitable method for joining topsheet 12 and backsheet 18 together is by a seal that forms border segment 20. As shown in FIG. 1, the inner portion of this border segment 20 defines a perimeter 22. Perimeter 22 encircles the secondary topsheet 14 and absorbent member 16. Border segment 20 is generally relatively narrow, and can extend a distance of approximately 0.25 to 6 mm. and preferably is approximately 3 mm. wide. However, the width of border 20 can be uniform or vary about the perimeter of pad 10. Border 20 provides a fluid impermeable seal that surrounds perimeter 22. The seal is preferably formed by the simultaneous application of pressure, with or without heat, to melt topsheet 12 and backsheet 18, thereby forming border segment 20.

In addition to providing fluid acquisition benefits, the secondary topsheet 14 may enhance the integrity of the product by stabilizing the positioning (e.g., by reducing bunching) of the fluid storage absorbent member 16. The secondary topsheet can include nonwoven or woven webs of synthetic fibers including polyester, polypropylene, or polyethylene; natural fibers including cotton or cellulose; blends of such fibers; or any equivalent materials or combinations of materials. Suitable secondary topsheets can also be made from mixtures of fibers with thermoplastic materials to form thermally bonded matrices. These thermoplastic materials can be in any of a variety of forms including particulates, fibers, or combinations of particulates and fibers. Thermoplastic fibers are a particularly preferred form because of their ability to form numerous interfiber bond sites. Other alternatives for the secondary topsheet are the use of wood pulp surface-sprayed with latex and air laid wood pulp structure bonded with latex.

The backsheet 18 is impervious to fluids (e.g., menses) and is preferably manufactured from a thin plastic film, although other flexible liquid impervious materials may also be used. As used herein, the term "flexible" refers to materials that are compliant and will readily conform to the general shape and contours of the human body. The backsheet 18 prevents the exudates absorbed and contained in the absorbent structure from wetting articles that contact the sanitary napkin 10 such as pants, pajamas and undergarments. The backsheet 18 can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet 18 can permit vapors to escape from the absorbent core (i.e., is breathable) while still preventing exudates from passing through the backsheet 18.

The topsheet 12 is compliant, soft feeling, and non-irritating to the wearer's skin. Further, the topsheet 12 is fluid pervious permitting fluids (e.g., menses) to readily penetrate through its thickness. A suitable topsheet 12 can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Preferred topsheets for use in the present are selected from high loft nonwoven topsheets and aperture formed film topsheets. Apertured formed films are especially preferred for the topsheet because they are pervious to body exudates and yet nonabsorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson), issued Dec. 30, 1975; U.S. Pat. No. 4,324,246 (Mullane, et al.), issued Apr. 13, 1982; U.S. Pat. No. 4,342,314 (Radel, et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Each of these patents are incorporated herein by reference. Particularly preferred microapetured formed film topsheets are disclosed in U.S. Pat. No. 4,609,518 (Curro et al), issue Sep. 2, 1986 and U.S. Pat. No. 4,629,643 (Curro et al), issued Dec. 16, 1986, which are incorporated by reference. The preferred topsheet for the present invention is the formed film described in one or more of the above patents and marketed on sanitary napkins by The Procter & Gamble Company of Cincinnati, Ohio as "DRI-WEAVE."

The body surface of the formed film topsheet can be hydrophilic so as to help liquid to transfer through the topsheet faster than if the body surface was not hydrophilic so as to diminish the likelihood that menstrual fluid will flow off the topsheet rather than flowing into and being absorbed by the absorbent structure. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated by reference. Alternatively, the body surface of the topsheet can be made hydrophilic by treating it with a surfactant such as is described in the above referenced U.S. Pat. No. 4,950,254, incorporated herein by reference.

In a preferred embodiment, where a thick catamenial pad is desired, a filler material can be positioned between the fluid storage absorbent member 16 and the backsheet 18. Useful filler materials, many of which are known in the art, include but are not limited to airfelt (e.g., chemi-thermomechanical pulp, southern softwood craft, recycled pulp), foams (e.g., polyurethane, cellulose, polystyrene), sawdust, paper wadding, recycled newspaper, etc. Alternatively, the foam materials of the present invention can be cut in layers of sufficient thickness to provide increased product thickness, typically between about 1 and about 2 cm.

In use, pad 10 can be held in place by any support or attachment device (not shown) well-known for such purposes. Preferably, pad 10 is placed in the user's undergarment or panty and secured thereto by a fastener such as an adhesive. The adhesive provides a means for securing the pad in the crotch portion of the panty. Thus, a portion or all of the outer surface of the backsheet 18 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before pad 10 is placed in use, the pressure-sensitive adhesive is typically covered with a removable release liner in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. The pad 10 is put in use by removing the release liner and thereafter placing the pad in a panty so that the adhesive contacts the panty. The adhesive maintains the pad 10 in its position within the panty during use.

The absorbent foams of the present invention are also useful as the upper acquisition/distribution component in a "multi-layer" absorbent core that additionally contains a lower fluid storage/redistribution component, where the absorbent core is positioned between the topsheet and backsheet to form the catamenial pad. For purposes of the present invention, an "upper" layer of a multi-layer absorbent core is a layer that is relatively closer to the body of the wearer, e.g., the layer closest to the topsheet. The term "lower" layer conversely means a layer of a multi-layer absorbent core that is relatively further away from the body of the wearer, e.g., the layer closest to the backsheet. This lower fluid storage/redistribution layer is typically positioned within the absorbent core so as to underlie the (upper) fluid acquisition/distribution layer and be in fluid communication therewith. This lower storage/redistribution layer can comprise a variety of fluid storage/redistribution components including those containing absorbent gelling materials such as disclosed in U.S. Pat. No. 5,061,259 (Goldman et. al), issued Oct. 29, 1991, U.S. Pat. No. 4,654,039 (Brandt et al), issued Mar. 31, 1987 (reissued Apr. 19, 1988 as Re. U.S. Pat. No. 32,649), U.S. Pat. No. 4,666,983 (Tsubakimoto et al), issued May 19, 1987, and U.S. Pat. No. 4,625,001 (Tsubakimoto et al), issued Nov. 25, 1986, all of which are incorporated by reference; absorbent macrostructures made from these absorbent gelling materials such as those disclosed in U.S. Pat. No. 5,102,597 (Roe et al), issued Apr. 7, 1992, and U.S. Pat. No. 5,324,561 (Rezai et al), issued Jun. 23, 1994, both of which are incorporated by reference); and absorbent gelling materials laminated between two tissue layers such as those disclosed in U.S. Pat. No. 4,260,443 (Lindsay et al), issued Apr. 7, 1981, U.S. Pat. No. 4,467,012 (Pedersen et al), issued Aug. 21, 1984, U.S. Pat. No. 4,715,918 (Lang), issued Dec. 29, 1987, U.S. Pat. No. 4,851,069 (Packard et al), issued Jul. 25, 1989, U.S. Pat. No. 4,950,264 (Osborn), issued Aug. 21, 1990; U.S. Pat. No. 4,994,037 (Bernardin), issued Feb. 19, 1991; U.S. Pat. No. 5,009,650 (Bernardin), issued Apr. 23, 1991; U.S. Pat. No. 5,009,653 (Osborn), issued Apr. 23, 1991; U.S. Pat. No. 5,128,082 (Makoui), Jul. 7, 1992; U.S. Pat. No. 5,149,335 (Kellenberger et al), issued Sep. 22, 1992; and U.S. Pat. No. 5,176,668 (Bernardin), issued Jan. 5, 1993, all of which are incorporated by reference.

There is no particular criticality with respect to the positional relationship of the fluid acquisition/distribution foam component and the fluid storage/redistribution component within these multi-layer absorbent cores so long as these components are in effective fluid communication with each other and so long as each component is large enough to effectively hold and/or transport the amount of aqueous body fluid that is expected to be discharged into the catamenial pad. The most preferred relationship between the fluid acquisition/distribution foam component and the fluid storage/redistribution component within the absorbent core is to place these components in a layered configuration. In such a layered configuration, the fluid acquisition/distribution foam component comprises an upper foam layer which overlies a subjacent fluid storage/redistribution component in the form of a lower layer. It should be understood that these two types of layers refer merely to the upper and lower zones of the absorbent core and are not necessarily limited to single layers or sheets. Both the fluid acquisition/distribution zone, e.g., upper layer, and the fluid storage/redistribution zone, e.g., lower layer, can comprise several layers the requisite type. Thus, as used herein, the term "layer" includes the terms "layers" and "layered".

B. Bandages and Wound Dressings

Absorbent foams of the present invention are also useful in bandages and dressings for wounds. These include articles ranging from simple bandaids to large surgical dressings and bandages. A bandage or dressing can simply comprise a topsheet, an absorbent foam of the present invention, and a fluid impervious backsheet optionally attached to adhesive strips in various shapes and sizes. The foams of the present invention are particularly good at absorbing fluids from suppurating wounds and preventing or reducing contact of the healing area with media that are conducive to microbiological growth. Potential wound healing benefits can be conferred by pretreating the absorbent foam with any of a wide variety of antimicrobial and/or antiseptic compounds well know to those skilled in the art.

C. Surgical Drapes

Absorbent foams of the present invention are also useful in surgical drapes. These are sheets of material that catch blood during surgical procedures. They typically comprise a thin layer of absorbent material, in this case the foam of the present invention, a fluid impervious backsheet, typically a 1–2 mil thick sheet of polyethylene. The polyethylene can optionally be treated with an adhesive to secure its placement in surgery. The foam of the present invention is particularly easy to form into such articles. Further, the inherent integrity of such foams prevents contamination of the area by loose materials such as might be found in traditional fiber-based absorbent structures. The absorbent properties are well suited to capturing splattered blood quickly and preventing its spread, e.g. to the floor thus producing a slipping hazard. Smaller sizes of these laminates may also be used as wipes for blood and blood based fluids.

V. Test Methods for Polymeric Foams

A. Vertical Wicking Capability

1. Preparation of Artificial Menstrual Fluid

Artificial Menstrual Fluid (AMF) is prepared by combining equal volumes of gastric mucin solution and fresh, sterile defibrinated sheep blood (Cleveland Scientific, American Biomedical, Bath, Ohio). The gastric mucin solution is prepared by combining the following in the proportions and order shown:

450 mL of aqueous sodium dihydrogen phosphate (0.138 wt. %) solution containing sodium chloride (0.85 wt. %) adjusted to pH 7.2±0.1;

7.5 mL potassium hydroxide aqueous solution;

31 g sterilized gastric mucin (ICN Biomedical Inc., Cleveland, Ohio); heated 2.5 hours to completely dissolve the gastric mucin. The solution is allowed to cool to less than 40° C.;

2.0 mL of 8 wt. % aqueous lactic acid solution.

The mixture is autoclaved at 121° C. for 15 minutes, then allowed to cool to room temperature. This mixture should be refrigerated and should be used within 7 days.

2. Sample Preparation

Foam samples are cut into 2.54 cm width strips about 25 cm long. Two samples are cut for each material to be tested. The samples are sealed in plastic on the top and on both long sides using a T-Bar sealer (Model T-7, 115VAC, 65 W Harwil Company, Santa Monica, Calif.). The 0.5 centimeter at the bottom of the material strip remains exposed. The outside of the plastic is graduated with marks each centimeter along the length of the sample, starting at the bottom of the plastic (not the bottom of the sample).

3. Equipment Preparation

The AMF is stirred for 30 minutes at 22° C. Approximately 300 mL of the equilibrated AMF is poured into a 500 mL recrystallizing dish. The filled dish is stirred magnetically at low speed.

A cylindrical Plexiglas bar (30.5 cm cylindrical bar with at least two attached Plexiglas plates (25 cm×0.5 cm×3 cm) attached at the end with the spacing being adjustable) is clamped onto a ring stand. The clamp should tentatively be set approximately 18–20 inches above the base of the stand. Allow enough space between the Plexiglas plates on the end of the cylindrical bar is provided to fit the thickness of the samples to be tested.

4. Test Procedure

The sealed top side of the sample is placed between two of the Plexiglas plates, and then the plates are tightened together until the sample is completely suspended. There should be enough room along the width of the plates to fit 2–3 samples without the samples touching. If not, additional plates can be used to position the samples one behind the other. After suspending all samples, the bottom and top of the samples should all be level with respect to the Plexiglas plates and each other.

The stir plate and dish of AMF is placed directly underneath the suspended samples. The samples are lowered such that 0.5 cm of each sample is submerged in the AMF. (The plastic covered portion of the samples should not be submerged, as fluid will tend to wick in the interfaces of the seal instead of within the sample). Adjustments to level the bar and samples are made, if necessary, so that each sample bottom is equally submerged in the AMF.

The absorbent foam samples are suspended in the stirred AMF to the bottom of the plastic. The time elapsed when the fluid height reaches each 1 cm marking is recorded. The average height of the fluid front in these samples is approximated. The heterogeneity within the samples provides channels of wicked fluid with no clear leading edge. The midpoint of the wicked height is taken as the value to be recorded. The average of the final vertical wicking values recorded for the samples (n=2) is used as the vertical wicking value for the material. At the conclusion of the measurement, the sample is sectioned into 1 cm pieces and weighed to obtain (after subtraction of the weight of the sample) the capacity of the material at varying heights.

B. Horizontal Gravimetric Wicking

Horizontal Gravimetric Wicking (HGW) is an absorbency test that measures the uptake of fluid by a 2.5 in by 7.5 in absorbent member or catamenial pad sample as a function of time. In this method, the sample is held upside down horizontally in a holder suspended from an electronic balance. A glass supply tube, containing the test fluid (in this case, AMF at 22° C.) and connected to a fluid reservoir at zero hydrostatic head relative to the test sample, is allowed to contact the lower surface of the sample as a point source and the increase in weight of the sample is used as a measure of fluid uptake versus time. The test proceeds for 3900 seconds. During the test, the sample is constrained under 0.18 psi (1.2 kPa) pressure by a conformable water-filled plastic bag covered by a metal weight. This conformable system provides a hydrostatic pressure to the sample to allow the pressure on the sample to remain relatively constant over the entire sample area.

"Initial Uptake" is defined as the weight of AMF absorbed by the system after 3900 seconds. "Rewet" is subsequently measured on the absorbent member or catamenial pad to find out the amount of fluid that can be repeatedly blotted from the structure/pad with Whatman filter paper at 0.25 psi (1.7 kPa) until the core will give up less than 0.5 g of AMF. "Retained Uptake" is calculated as the difference between "Initial Uptake" and "Rewet".

C. Resistance to Compression Deflection (RTCD)

Resistance to compression deflection can be quantified by measuring the amount of strain (% reduction in thickness) produced in a foam sample which has been saturated with synthetic urine, after a confining pressure of 0.74 psi (5.1 kPa) has been applied to the sample.

Jayco synthetic urine used in this method is prepared by dissolving a mixture of 2.0 g KCl, 2.0 g $Na_2SO_4$, 0.85 g $NH_4H_2PO_4$, 0.15 g $(NH_4)_2HPO_4$, 0.19 g $CaCl_2$, and 0.23 g $MgCl_2$ to 1.0 liters with distilled water. The salt mixture can be purchased from Endovations, Reading, Pa. (cat No. JA-00131-000-01).

The foam samples, synthetic urine and equipment used to make measurements are all equilibrated to a temperature of 31° C. All measurements are also performed at this temperature.

A foam sample sheet is saturated to its free absorbent capacity by soaking in a bath of synthetic urine. After 3 minutes, a cylinder having a 1.0 $in^2$ (6.5 $cm^2$) circular surface area is cut out of the saturated, expanded sheet with a sharp circular die. The cylindrical sample is soaked in synthetic urine at 31° C. for a further 6 minutes. The sample is then removed from the synthetic urine and is placed on a flat granite base under a gauge suitable for measuring the sample thickness. The gauge is set to exert a pressure of 0.08 psi (0.6 kPa) on the sample. Any gauge fitted with a foot having a circular surface area of at least 1 $in^2$ (6.5 $cm^2$) and capable of measuring thickness to 0.001 in (0.025 mm) can be employed. Examples of such gauges are an Ames model 482 (Ames Co.; Waltham, Mass.) or an Ono-Sokki model EG-225 (Ono-Sokki Co., Ltd.; Japan).

After 2 to 3 min., the expanded thickness (X1) is recorded. A force is then applied to the foot so that the saturated foam sample is subjected to a pressure of 0.74 psi (5.1 kPa) for 15 minutes. At the end of this time, the gauge is used to measure the final sample thickness (X2). From the initial and final thickness measurements, the percent strain induced can be calculated for the sample as follows: $|(X1-X2)/X1|\times 100$=% reduction in thickness.

D. Free Absorbent Capacity

Free absorbent capacity can be quantified by measuring the amount of synthetic urine absorbed in a foam sample which has been saturated with synthetic urine.

The foam samples and synthetic urine are equilibrated to a temperature of 31° C. Measurements are performed at ambient temperature.

A foam sample sheet is saturated to its free absorbent capacity by soaking in a bath of synthetic urine. After 3 minutes, a cylinder having a 1.0 in$^2$ (6.5 cm$^2$) circular surface area is cut out of the saturated sheet with a sharp circular die. The cylindrical sample is soaked in synthetic urine at 31° C. for a further 3 minutes. The sample is then removed from the synthetic urine and is placed on a digital balance. Any balance fitted with a weighing pan having an area larger than that of the sample and with a resolution of 1 milligram or less can be employed. Examples of such balances are the Mettler PM 480 and Mettler PC 440 (Mettler Instrument Corp; Hightstown N.J.).

After determining the weight of the wet foam sample (Ww), it is placed between 2 fine plastic mesh screens on top of 4 disposable paper towels. The sample is squeezed 3 times by firmly rolling a plastic roller over the top screen. The sample is then removed, soaked in distilled water for approximately 2 minutes, and squeezed between mesh screens as before. It is then placed between 8 layers of disposable paper towels (4 on each side) and pressed with 20,000 lbs. of force in a Carver Laboratory Press. The sample is then removed from the paper towels, dried in a Fisher convection oven at 82° C. for 20 minutes, and its dry weight recorded (Wd).

The free absorbent capacity (FAC) is the wet weight (Ww), less the dry weight (Wd) divided by the dry weight (Wd), i.e., FAC=[(Ww−Wd)/Wd]

E. Dynamic Mechanical Analysis (DMA)

DMA is used to determine the Tgs of polymers including polymeric foams. Samples of the foams are sliced into blocks 3–5 mm in thickness and washed 3–4 times in distilled water, expressing the fluid through roller nips between each washing. The resulting foam blocks are allowed to dry in air. The dried foam slices are cored to yield a cylinders 25 mm in diameter. These cylinders are analyzed using a Rheometrics RSA-II dynamic mechanical analyzer set in compression mode using parallel plates 25 mm in diameter. Instrument parameters used were as follows:

Temperature step from ca. 85° C. to −40° C. in steps of 2.5° C.

Soak intervals between temperature changes of 125–160 seconds

Dynamic strain set at 0.1% to 1.0% (usually 0.7%)

Frequency set at 1.0 radians/second

Autotension set in static force tracking dynamic force mode with initial static force set at 5 g.

The glass transition temperature is taken as the maximum point of the loss tangent versus temperature curve.

VI. Specific Examples

These examples illustrate the specific preparation of collapsed HIPE foams according to the present invention.

EXAMPLE 1

Preparation of Foam from a HIPE

A) HIPE Preparation

Anhydrous calcium chloride (36.32 kg) and potassium persulfate (567 g) are dissolved in 378 liters of water. This provides the water phase stream to be used in a continuous process for forming a HIPE emulsion.

To a monomer combination comprising 400 g styrene, 2900 g divinylbenzene (40% divinylbenzene and 60% ethyl styrene), and 4800 g 2-ethylhexylacrylate is added 480 g of high purity diglycerol monooleate and Tinuvin 765 [bis(1, 2,2,5,5-pentamethylpiperidinyl)sebacate] antioxidant (41 g).

This diglycerol monooleate emulsifier is prepared following the general procedure for preparing polyglycerol esters described in U.S. Pat. No. 5,387,207 (Dyer et al.) issued Feb. 7, 1995. A polyglycerol composition comprising approximately 97% or greater diglycerol and 3% or less triglycerol (Solvay Performance Chemicals; Greenwich, Conn.) is esterified with fatty acids having a fatty acid composition comprising approximately 71% C18:1, 4% C18:2, 9% C16:1, 5% C16:0, and 11% other fatty acids (Emersol-233LL; Emery/Henkel) in a weight ratio of 62:38, using sodium hydroxide as a catalyst at about 225° C. under conditions of mechanical agitation, nitrogen sparging, and gradually increasing vacuum, with subsequent phosphoric acid neutralization, cooling to about 85° C., and settling to reduce the level of unreacted polyglycerols. The polyglycerol ester reaction product is first fractionally distilled through two CMS-15A centrifugal molecular stills connected in series to reduce the levels of unreacted polyglycerols and fatty acids and then redistilled through the stills to yield distillation fractions high in diglycerol monoesters. Typical conditions for the final distillation pass are a feed rate of about 15 lb/hr, a degasser vacuum of about 21–26 microns, a bell jar vacuum of about 6–12 microns, a feed temperature of about 170° C., and a residue temperature of about 180° C. Distillation fractions high in diglycerol monoesters are combined, yielding a reaction product (as determined by supercritical fluid chromatography) comprising approximately 50% diglycerol monooleate, 27% other diglycerol monoesters, 20% polyglycerols, and 3% other polyglycerol esters. After mixing, the reaction product is allowed to settle overnight. The supernatant is withdrawn and used in the oil phase as the emulsifier in forming the HIPE. (About 20 g of a sticky residue is discarded.)

Separate streams of the oil phase (25° C.) and water phase (65°–70° C.) are fed to a dynamic mixing apparatus. Thorough mixing of the combined streams in the dynamic mixing apparatus is achieved by means of a pin impeller. At this scale of operation, an appropriate pin impeller comprises a cylindrical shaft of about 21.6 cm in length with a diameter of about 1.9 cm. The shaft holds 4 rows of pins, 2 rows having 17 pins and 2 rows having 16 pins, each having a diameter of 0.5 cm extending outwardly from the central axis of the shaft to a length of 1.6 cm. The pin impeller is mounted in a cylindrical sleeve which forms the dynamic mixing apparatus, and the pins have a clearance of 0.8 mm from the walls of the cylindrical sleeve.

A spiral static mixer is mounted downstream from the dynamic mixing apparatus to provide back pressure in the dynamic mixer and to provide improved incorporation of components into the emulsion that is eventually formed. Such a static mixer is 14 inches (35.6 cm) long with a 0.5 inch (1.3 cm) outside diameter. The static mixer is a TAH Industries Model 070-821, modified by cutting off 2.4 inches (6.1 cm).

The combined mixing apparatus set-up is filled with oil phase and water phase at a ratio of 2 parts water to 1 part oil. The dynamic mixing apparatus is vented to allow air to escape while filling the apparatus completely. The flow rates during filling are 3.78 g/sec oil phase and 7.56 cc/sec water phase.

Once the apparatus set-up is filled, agitation is begun in the dynamic mixer, with the impeller turning at 800 RPM.

The flow rate of the water phase is then steadily increased to a rate of 44.1 cc/sec in a time period of about 30 sec. and the oil phase flow rate is reduced to 1.25 g/sec over a time period of about 1 min. The back pressure created by the dynamic and static mixers at this point is 2 psi (14 kPa). The resultant HIPE has a water-to-oil ratio of about 50:1.

B) Polymerization/Curing of HIPE

The HIPE from the static mixer is collected in a round polypropylene tub, 17 in. (43 cm) in diameter and 7.5 in. (10 cm) high, with a concentric insert made of Celcon plastic. The insert is 5 in. (12.7 cm) in diameter at its base and 4.75 in (12 cm) in diameter at its top and is 6.75 in. (17.14 cm) high. The HIPE-containing tubs are kept in a room maintained at 65° C. for 18 hours to cure and provide a polymeric HIPE foam.

C) Foam Washing and Dewatering

The cured HIPE foam is removed from the tubs. The foam at this point has residual water phase (containing dissolved emulsifiers, electrolyte, initiator residues, and initiator) about 32–38 times (32–38×) the weight of polymerized monomers. The foam is sliced with a sharp reciprocating saw blade into sheets which are 0.15 inches (0.38 cm) in thickness. These sheets are then subjected to compression in a series of 2 porous nip rolls equipped with vacuum which gradually reduces the residual water phase content of the foam to about 2 times (2×) the weight of the polymerized monomers. At this point, the sheets are then resaturated with a 1% solution of Pegosperse 200 ML in water at 60° C. and are squeezed in a series of 3 porous nip rolls equipped with vacuum to a water phase content of about 4X. The CaCl$_2$ content of the foam is below 2%.

The HIPE foam is then dried in air for about 16 hours. Such drying reduces the moisture content to about 4–10% by weight of polymerized material.

EXAMPLE 2

Preparation of Foams from HIPEs

HIPE foams are prepared using various pour temperatures, cure times and temperatures, water to oil (W:O) ratios, and impeller mixer speeds. These foams and their properties are shown in Tables 1 and 2 below:

TABLE 1

Hole Sizes vs. Pour Temperature

| Example | Pour Temp (°C.) | Mixer Speed (rpm) | W:O Ratio | Cure Temp (°C.) | Cure Time (hrs) | Hole Size (μ) |
|---|---|---|---|---|---|---|
| 2a | 65° | 800 | 45:1 | 65° | 16 | 11.8 |
| 2b | 74° | 800 | 50:1 | 65° | 16 | 13.8 |
| 2c | 65° | 800 | 50:1 | 65° | 16 | 11.7 |
| 2d | 65° | 800 | 55:1 | 65° | 16 | 11.1 |
| 2e | 82° | 800 | 50:1 | 82° | 2 | 17.4 |
| 2f | 82° | 800 | 45:1 | 82° | 2 | 16.4 |

TABLE 2

Foam Capacity and Strength vs. W:O Ratio

| Example | W:O Ratio | RTCD % | FAC g/g |
|---|---|---|---|
| 1a | 45:1 | 32.3% | 44.7 |
| 1b | 50:1 | 55.7% | 46.0 |
| 1c | 50:1 | 57.0% | 50.1 |

TABLE 2-continued

Foam Capacity and Strength vs. W:O Ratio

| Example | W:O Ratio | RTCD % | FAC g/g |
|---|---|---|---|
| 1d | 55:1 | 64.9% | 52.7 |
| 1e | 50:1 | 68.8% | 49.2 |
| 1f | 45:1 | 54.5% | 43.0 |

Table 3 shows the effect on the vertical wicking rate and capacity of residual calcium chloride salt in the foam relative to a washed foam sample that has been rehydrophilized according to the present invention. The foam sample labeled "Unwashed" is the unwashed HIPE foam of Example 2b containing residual calcium chloride salt. The foam sample labeled "Washed" is the HIPE foam of Example 2b that has been washed to remove the salt and rehydrophilized with PEGOSPERSE 200 ML. The columns relating to "Wicking Rate" show the time required to wick AMF to the indicated heights. The columns relating to "Capacity" show the amount of AMF wicked to that height after a period of 18 hours:

TABLE 3

Wicking Rate and Capacity at Equilibrium Height

| Height (cm) | Wicking Rate | | Capacity | |
|---|---|---|---|---|
| | Unwashed (min) | Washed (min) | Unwashed (g/g) | Washed (g/g) |
| 1 | 8.3 | .5 | 53.0 | 45.9 |
| 2 | 15.3 | 1.2 | 41.5 | 50.5 |
| 3 | 25.5 | 3.5 | 45.7 | 48.6 |
| 4 | 40.5 | 6.5 | 40.0 | 42.2 |
| 5 | 85 | 13 | 40.3 | 44.5 |
| 6 | 120 | 30 | 39.2 | 42.4 |
| 7 | | | 33.3 | 39.5 |
| 8 | | | 19.1 | 22.7 |
| 9 | | | 4.6 | 5.4 |
| 10 | | | 0.8 | 1.6 |
| 11 | | | 0.0 | 0.4 |
| 12 | | | 0.0 | 0.0 |

Table 3 above shows that removal of the calcium chloride salt speeds up the wicking rate without adversely affecting capacity.

Table 4 shows the effect on Horizontal Gravimetric Wicking (HGW) of residual calcium chloride salt in the foam relative to a washed foam sample that has been rehydrophilized according to the present invention. The foam sample labeled "Unwashed" is the unwashed HIPE foam of Example 2b containing residual calcium chloride salt. The foam sample labeled "Washed" is the HIPE foam of Example 2b that has been washed to remove the salt and rehydrophilized with PEGOSPERSE 200 ML.:

TABLE 4

| | HGW | | |
|---|---|---|---|
| Foam Sample | Initial Uptake (g/g) | Retained Uptake (g/g) | % Retained/Initial Uptake |
| Unwashed | 14 | 12 | 86% |
| Washed | 24 | 19 | 79% |

Table 4 above shows that the presence calcium chloride in the foam inhibits the HGW, relative to the same foam that has been washed and rehydrophilized.

EXAMPLE 3

Preparation of Foams from HIPEs

HIPE foams are prepared according to the procedure of Example 1. The HIPEs are poured at 74° C. and 800 RPM and cured at 82° C. for 2 hours. Differences in water to oil (W:O) ratio and corresponding differences in properties are shown in Table 5.

TABLE 5

Foam Capacity and Strength vs. W:O Ratio

| Example | W:O Ratio | RTCD % | FAC g/g |
|---|---|---|---|
| 3a | 30:1 | 5.7% | 29.8 |
| 3b | 40:1 | 22.5% | 39.4 |
| 3c | 40:1 | 12.0% | 39.6 |
| 3d | 50:1 | 59.2% | 47.2 |

EXAMPLE 4

Preparation of Barrier Layer from HIPEs

A foam material useful as the optional barrier layer is prepared according to the general process described in Example 1. The only modifications needed to obtain the relatively smaller cell and hole sizes desired for the barrier layer are mixing at a temperature of 156° F. and using a mixer speed of about 1300 RPM.

EXAMPLE 5

Catamenial Pad Having A Foam Absorbent Member

A piece of polymeric foam according to any of Examples 2a–2f is cut into a strip having a width of 6.4 cm, a length of 19 cm, and a thickness of 0.51 cm (volume=62 cc). This piece of foam is positioned as an absorbent member or layer between a fluid impervious backsheet and an apertured film topsheet (such as DRI-WEAVE). Optionally, a nonwoven sheet can be used as the topsheet in place of the apertured film. Preferably, a secondary topsheet is positioned between the foam absorbent member and the apertured topsheet.

EXAMPLE 6

Catamenial Pad Having Two Foam Absorbent Members

A piece of polymeric foam according to any of Examples 2a, 2b, 2c, or 2d is cut into a strip having a width of 6.4 cm, a length of 10 cm, and a thickness of 0.19 cm (volume=12 cc). A second piece of polymeric foam according to Examples 1e or 1f is cut into a strip having a width of 6.4 cm, a length of 19 cm, and a thickness of 0.19 cm (volume 23 cc). The pieces are assembled as described in Example 5 into a catamenial pad with the upper layer (adjacent to the topsheet) being the smaller of the two pieces of foam. Preferably the two foam pieces are lightly bonded together with any suitable bonding adhesive applied in specific points to maintain contact between the pieces without restricting fluid flow.

EXAMPLE 7

Catamenial Pad Having a Barrier Layer

A catamenial pad having an absorbent core comprising three absorbent foams of the present invention and a filler material between the foam absorbent core and the backsheet is prepared as follows. A piece of polymeric foam according to any of Examples 2a, 2b, 2c, or 2d is cut into a strip which will be the upper layer (adjacent the topsheet) of the absorbent core. A second piece of polymeric foam according to Examples 1e or 1f is cut into a strip that will be the middle layer of the absorbent core. A third piece of polymeric foam according to Example 4 is cut into a strip that will be the barrier layer (adjacent the filler material, which is optionally airfelt) of the absorbent core. This barrier layer will have a number average cell size of from about 15 to about 50 µm and a number average hole size of from about 4 to about 9 µm.

For a thick product, the filler material (e.g., airfelt) is located between the absorbent core and the backsheet. The pieces are assembled as described in Example 5 into a catamenial pad. Preferably the three foam pieces are lightly bonded together with any suitable bonding adhesive applied in specific points to maintain contact between the pieces without restricting fluid flow.

EXAMPLE 8

Catamenial Pad Containing Foam and Absorbent Gelling Material

A piece of polymeric foam according to any of Examples 2a, 2b, 2c, or 2d is cut into a strip having a width of 6.4 cm, a length of 10 cm, and a thickness of 0.19 cm (volume=12 cc). This is assembled over a web consisting of cellulosic fibers and absorbent gelling material or absorbent gelling material laminated between two layers of tissue.

EXAMPLE 9

Bandage Having Foam Component

Any of the foams of Example 2 can be cut into a piece 2.5 cm square and 0.2 cm thick. This piece of foam is attached to a fluid impermeable backsheet strip having a width of 2.8 cm and a length of 7 cm using an adhesive. The exposed edges of this strip are coated with any suitable contact adhesive and cover with a release paper and packaged in a sanitary wrapper. Optionally, a fluid pervious topsheet such as DRI-WEAVE or a nonwoven can be attached on top of the foam.

EXAMPLE 10

Surgical Drape Having Foam Component

Any of the foams of Example 2 can be sliced into a piece 1 m square and 0.13 cm thick. This piece of foam is attached to a 1 m square fluid impermeable backsheet using any suitable adhesive. The opposing side of the backsheet can be treated with any suitable contact adhesive and covered with release paper so as to provide for stability in application to a particular area when in use.

EXAMPLE 11

Tampon Having Foam Component

Any of the foams of Example 2 can be cored to provide a tube having a radius of 1.2 cm and a length of 8 cm. The tube is wrapped in a fluid permeable nonwoven coversheet and attached to a string for easy removal.

What is claimed is:

1. A polymeric foam material which is capable of absorbing blood and blood-based fluids, said polymeric foam material comprising a hydrophilic, flexible, nonionic polymeric foam structure of interconnected open cells, which foam structure has:

A) the ability to wick artificial menstrual fluid (AMF) vertically to a height of 5 cm in less than about 60 minutes;

B) a capillary specific surface area in the range of from about 0.0080 to about 0.040 m²/cc;

C) a resistance to compression deflection of from about 5 to about 95% when measured under a confining pressure of 0.74 psi at 31° C. after 15 minutes;

D) a free absorbent capacity of from about 20 to about 125 g/g; and

E) less than about 2% residual hydratable salts.

2. The foam material of claim 1 wherein said foam structure has:

A) the ability to vertically wick AMF to a height of 5 cm in less than about 20 minutes;

B) a capillary specific surface area in the range of from about 0.010 to about 0.030 m²/cc;

C) a free absorbent capacity of from about 40 to about 70 g/g.

3. The foam material of claim 2 wherein said foam structure has:

B) a capillary specific surface area in the range of from about 0.012 to about 0.026 m²/cc.

4. The foam material of claim 3 wherein said foam structure has about 0.5% or less of said residual hydratable salts.

5. The foam material of claim 2 wherein said foam structure has the ability to wick at least about 30 g/g of AMF to a height of about 5 cm at equilibrium.

6. The foam material of claim 2 wherein said foam structure has % Retained/Initial Uptake of AMF of at least about 50%.

7. The foam material of claim 2 which has a number average cell size of from about 20 to about 180 μm and a number average hole size of from about 4 to about 30 μm.

8. The foam material of claim 7 which has a number average cell size of from about 35 to about 130 μm and a number average hole size of from about 10 to about 28 μm.

9. The foam material of claim 1 which has a dry basis density of from about 0.014 to about 0.024 g/cc.

* * * * *

UNITED STATES PATENT AND TRADEMARK OFFICE
CERTIFICATE OF CORRECTION

PATENT NO.    : 5,795,921                                      Page 1 of 1
DATED         : August 18, 1998
INVENTOR(S)   : John C. Dyer et al.

It is certified that error appears in the above-identified patent and that said Letters Patent is hereby corrected as shown below:

Column 14,
Line 57, "esterifing" should read -- esterifying --.

Column 15,
Line 53, "typos" should read -- types --.

Signed and Sealed this

Fifth Day of March, 2002

*Attest:*

*Attesting Officer*

JAMES E. ROGAN
*Director of the United States Patent and Trademark Office*